(12) United States Patent
Govey et al.

(10) Patent No.: US 10,631,903 B2
(45) Date of Patent: Apr. 28, 2020

(54) CLAVICLE FIXATION SYSTEM

(71) Applicant: GLOBUS MEDICAL, INC., Audubon, PA (US)

(72) Inventors: Peter Govey, Philadelphia, PA (US); Stephanie Wolfe, Hatfield, PA (US); Andrew Davison, Downingtown, PA (US)

(73) Assignee: Globus Medical Inc., Audubon, PA (US)

( * ) Notice: Subject to any disclaimer, the term of this patent is extended or adjusted under 35 U.S.C. 154(b) by 260 days.

(21) Appl. No.: 15/808,113

(22) Filed: Nov. 9, 2017

(65) Prior Publication Data

US 2018/0256224 A1  Sep. 13, 2018

Related U.S. Application Data

(63) Continuation-in-part of application No. 15/719,633, filed on Sep. 29, 2017.

(60) Provisional application No. 62/469,813, filed on Mar. 10, 2017.

(51) Int. Cl.
*A61B 17/80* (2006.01)

(52) U.S. Cl.
CPC ...... *A61B 17/8014* (2013.01); *A61B 17/8061* (2013.01); *A61B 17/8057* (2013.01)

(58) Field of Classification Search
CPC . A61B 17/80; A61B 17/8004; A61B 17/8014; A61B 17/8052; A61B 17/8057; A61B 17/8061
See application file for complete search history.

(56) References Cited

U.S. PATENT DOCUMENTS

| | | |
|---|---|---|
| 1,105,105 A | 7/1914 | Sherman |
| 2,486,303 A | 10/1949 | Longfellow |
| 3,716,050 A | 2/1973 | Johnston |
| 4,493,317 A | 1/1985 | Klaue |
| 4,524,765 A | 6/1985 | de Zbikowski |
| 4,651,724 A | 3/1987 | Berentey et al. |
| 4,683,878 A | 8/1987 | Carter |
| 4,781,183 A | 11/1988 | Casey et al. |
| 4,867,144 A | 9/1989 | Karas et al. |
| 5,002,544 A | 3/1991 | Klaue et al. |
| 5,041,114 A | 8/1991 | Chapman et al. |

(Continued)

FOREIGN PATENT DOCUMENTS

| | | |
|---|---|---|
| CN | 201987653 U | 9/2011 |
| CN | 202313691 U | 7/2012 |

(Continued)

*Primary Examiner* — Eric S Gibson

(57) ABSTRACT

Clavicle fixation devices and methods thereof. A clavicle fixation device includes an elongated plate extending between first and second ends, the elongated plate defining a plurality of spaced apart screw holes. At least one pair of relief cuts extends into the elongated plate on opposite sides thereof, the at least one pair of relief cuts axially positioned between a pair of the spaced apart screw holes and at least one pair of suture holes along opposite sides of the elongated plate, the at least one pair of suture holes axially positioned between a pair of the spaced apart screw holes. At least one pair of relief cuts is axially aligned with a pair of suture holes to define combined holes on opposite sides of the elongated plate.

15 Claims, 26 Drawing Sheets

(56) References Cited

U.S. PATENT DOCUMENTS

| | | | |
|---|---|---|---|
| 5,151,103 A | 9/1992 | Tepic et al. |
| 5,259,398 A | 11/1993 | Vrespa |
| 5,364,399 A | 11/1994 | Lowery et al. |
| 5,372,598 A | 12/1994 | Luhr et al. |
| 5,423,826 A | 6/1995 | Coates et al. |
| 5,601,553 A | 2/1997 | Trebing et al. |
| 5,676,667 A | 10/1997 | Hausman |
| 5,709,686 A | 1/1998 | Talos et al. |
| 5,718,704 A | 2/1998 | Medoff |
| 5,746,742 A | 5/1998 | Runciman et al. |
| 5,785,712 A | 7/1998 | Runciman et al. |
| 5,938,664 A | 8/1999 | Winquist et al. |
| 6,001,099 A | 12/1999 | Huebner |
| 6,096,040 A | 8/2000 | Esser |
| 6,107,718 A | 8/2000 | Schustek et al. |
| 6,152,927 A | 11/2000 | Farris et al. |
| 6,206,881 B1 | 3/2001 | Frigg et al. |
| 6,283,969 B1 | 9/2001 | Grusin et al. |
| 6,309,393 B1 | 10/2001 | Tepic et al. |
| 6,322,562 B1 | 11/2001 | Wolter |
| 6,364,882 B1 | 4/2002 | Orbay |
| 6,533,786 B1 | 3/2003 | Needham et al. |
| 6,623,486 B1 | 9/2003 | Weaver et al. |
| 6,669,700 B1 | 12/2003 | Farris et al. |
| 6,669,701 B2 | 12/2003 | Steiner et al. |
| 6,712,820 B2 | 3/2004 | Orbay |
| 6,719,759 B2 | 4/2004 | Wagner et al. |
| 6,730,091 B1 | 5/2004 | Pfefferle et al. |
| 6,866,665 B2 | 3/2005 | Orbay |
| 6,955,677 B2 | 10/2005 | Dahners |
| 6,974,461 B1 | 12/2005 | Wolter |
| 7,001,387 B2 | 2/2006 | Farris et al. |
| 7,063,701 B2 | 6/2006 | Michelson |
| 7,128,744 B2 | 10/2006 | Weaver et al. |
| 7,137,987 B2 | 11/2006 | Patterson et al. |
| 7,153,309 B2 | 12/2006 | Huebner et al. |
| 7,179,260 B2 | 2/2007 | Gerlach et al. |
| 7,250,053 B2 * | 7/2007 | Orbay ............... A61B 17/8057 606/291 |
| 7,294,130 B2 | 11/2007 | Orbay |
| 7,322,983 B2 | 1/2008 | Harris |
| 7,341,589 B2 | 3/2008 | Weaver et al. |
| 7,354,441 B2 | 4/2008 | Frigg |
| 7,604,657 B2 | 10/2009 | Orbay et al. |
| 7,632,277 B2 | 12/2009 | Woll et al. |
| 7,635,381 B2 | 12/2009 | Orbay |
| 7,637,928 B2 | 12/2009 | Fernandez |
| 7,655,029 B2 | 2/2010 | Niedernberger et al. |
| 7,695,472 B2 | 4/2010 | Young |
| 7,722,653 B2 | 5/2010 | Young et al. |
| 7,740,648 B2 | 6/2010 | Young et al. |
| 7,776,076 B2 | 8/2010 | Grady, Jr. et al. |
| 7,857,838 B2 | 12/2010 | Orbay |
| 7,867,260 B2 | 1/2011 | Meyer et al. |
| 7,867,261 B2 | 1/2011 | Sixto, Jr. et al. |
| 7,875,062 B2 | 1/2011 | Lindemann et al. |
| 7,905,910 B2 | 3/2011 | Gerlach et al. |
| 7,909,858 B2 | 3/2011 | Gerlach et al. |
| 7,951,178 B2 | 5/2011 | Jensen |
| 7,951,179 B2 | 5/2011 | Matityahu |
| 7,976,570 B2 | 7/2011 | Wagner et al. |
| D643,121 S | 8/2011 | Millford et al. |
| D646,785 S | 10/2011 | Milford |
| 8,043,297 B2 | 10/2011 | Grady, Jr. et al. |
| 8,057,520 B2 | 11/2011 | Ducharme et al. |
| 8,062,296 B2 | 11/2011 | Orbay et al. |
| 8,100,953 B2 | 1/2012 | White et al. |
| 8,105,367 B2 | 1/2012 | Austin et al. |
| 8,114,081 B2 | 2/2012 | Kohut et al. |
| 8,118,846 B2 | 2/2012 | Leither et al. |
| 8,162,950 B2 | 4/2012 | Digeser et al. |
| 8,167,918 B2 | 5/2012 | Strnad et al. |
| 8,177,820 B2 | 5/2012 | Anapliotis et al. |
| 8,246,661 B2 | 8/2012 | Beutter et al. |
| 8,252,032 B2 | 8/2012 | White et al. |
| 8,257,403 B2 | 9/2012 | Den Hartog et al. |
| 8,257,405 B2 | 9/2012 | Haidukewych et al. |
| 8,257,406 B2 | 9/2012 | Kay et al. |
| 8,262,707 B2 | 9/2012 | Huebner et al. |
| 8,267,972 B1 | 9/2012 | Gehlert |
| 8,317,842 B2 | 11/2012 | Graham et al. |
| 8,323,321 B2 | 12/2012 | Gradl |
| 8,337,535 B2 | 12/2012 | White et al. |
| 8,343,155 B2 | 1/2013 | Fisher et al. |
| 8,382,807 B2 | 2/2013 | Austin et al. |
| 8,394,098 B2 | 3/2013 | Orbay et al. |
| 8,394,130 B2 | 3/2013 | Orbay et al. |
| 8,398,685 B2 | 3/2013 | McGarity et al. |
| 8,403,966 B2 * | 3/2013 | Ralph ............... A61B 17/80 606/280 |
| 8,419,775 B2 | 4/2013 | Orbay et al. |
| 8,435,272 B2 | 5/2013 | Dougherty et al. |
| 8,439,918 B2 | 5/2013 | Gelfand |
| 8,444,679 B2 | 5/2013 | Ralph et al. |
| 8,491,593 B2 | 7/2013 | Prien et al. |
| 8,506,608 B2 | 8/2013 | Cerynik et al. |
| 8,512,385 B2 | 8/2013 | White et al. |
| 8,518,090 B2 | 8/2013 | Huebner et al. |
| 8,523,862 B2 | 9/2013 | Murashko, Jr. |
| 8,523,919 B2 | 9/2013 | Huebner et al. |
| 8,523,921 B2 | 9/2013 | Horan et al. |
| 8,551,095 B2 * | 10/2013 | Fritzinger ......... A61B 17/8014 606/280 |
| 8,568,462 B2 | 10/2013 | Sixto, Jr. et al. |
| 8,574,268 B2 | 11/2013 | Chan et al. |
| 8,597,334 B2 | 12/2013 | Mocanu |
| 8,603,147 B2 | 12/2013 | Sixto, Jr. et al. |
| 8,617,224 B2 | 12/2013 | Kozak et al. |
| 8,632,574 B2 | 1/2014 | Kortenbach et al. |
| 8,641,741 B2 | 2/2014 | Murashko, Jr. |
| 8,641,744 B2 | 2/2014 | Weaver et al. |
| 8,663,224 B2 | 3/2014 | Overes et al. |
| 8,728,082 B2 | 5/2014 | Fritzinger et al. |
| 8,728,126 B2 | 5/2014 | Steffen |
| 8,740,905 B2 | 6/2014 | Price et al. |
| 8,747,442 B2 | 6/2014 | Orbay et al. |
| 8,764,751 B2 | 7/2014 | Orbay et al. |
| 8,764,808 B2 | 7/2014 | Gonzalez-Hernandez |
| 8,777,998 B2 | 7/2014 | Daniels et al. |
| 8,790,376 B2 | 7/2014 | Fritzinger et al. |
| 8,790,377 B2 | 7/2014 | Ralph et al. |
| 8,808,333 B2 | 8/2014 | Kuster et al. |
| 8,808,334 B2 | 8/2014 | Strnad et al. |
| 8,834,532 B2 | 9/2014 | Velikov et al. |
| 8,834,537 B2 | 9/2014 | Castanada et al. |
| 8,852,246 B2 | 10/2014 | Hansson |
| 8,852,249 B2 | 10/2014 | Ahrens et al. |
| 8,864,802 B2 | 10/2014 | Schwager et al. |
| 8,870,931 B2 | 10/2014 | Dahners et al. |
| 8,888,825 B2 | 11/2014 | Batsch et al. |
| 8,906,076 B2 | 12/2014 | Mocanu et al. |
| 8,911,482 B2 | 12/2014 | Lee et al. |
| 8,926,675 B2 | 1/2015 | Leung et al. |
| 8,940,026 B2 | 1/2015 | Hilse et al. |
| 8,940,028 B2 | 1/2015 | Austin et al. |
| 8,940,029 B2 | 1/2015 | Leung et al. |
| 8,951,291 B2 | 2/2015 | Impellizzeri |
| 8,968,368 B2 | 3/2015 | Tepic |
| 9,011,457 B2 | 4/2015 | Grady, Jr. et al. |
| 9,023,052 B2 | 5/2015 | Lietz et al. |
| 9,050,151 B2 | 6/2015 | Schilter |
| 9,072,555 B2 | 7/2015 | Michel |
| 9,072,557 B2 | 7/2015 | Fierlbeck et al. |
| 9,107,678 B2 | 8/2015 | Murner et al. |
| 9,107,711 B2 | 8/2015 | Hainard |
| 9,107,713 B2 | 8/2015 | Horan et al. |
| 9,107,718 B2 | 8/2015 | Isch |
| 9,113,970 B2 | 8/2015 | Lewis et al. |
| 9,149,310 B2 * | 10/2015 | Fritzinger ......... A61B 17/8014 |
| 9,161,791 B2 | 10/2015 | Frigg |
| 9,161,795 B2 | 10/2015 | Chasbrummel et al. |
| 9,168,075 B2 | 10/2015 | Dell'Oca |
| 9,179,950 B2 | 11/2015 | Zajac et al. |
| 9,179,956 B2 | 11/2015 | Cerynik et al. |

(56) References Cited

U.S. PATENT DOCUMENTS

| | | | |
|---|---|---|---|
| 9,180,020 B2 | 11/2015 | Gause et al. | |
| 9,211,151 B2 | 12/2015 | Weaver et al. | |
| 9,259,217 B2 | 2/2016 | Fritzinger et al. | |
| 9,259,255 B2 | 2/2016 | Lewis et al. | |
| 9,271,769 B2 | 3/2016 | Batsch et al. | |
| 9,283,010 B2 | 3/2016 | Medoff et al. | |
| 9,295,506 B2 | 3/2016 | Raven, III et al. | |
| 9,314,284 B2 * | 4/2016 | Chan | A61B 17/1728 |
| 9,320,554 B2 * | 4/2016 | Greenberg | A61B 17/8061 |
| 9,322,562 B2 | 4/2016 | Takayama et al. | |
| 9,370,388 B2 | 6/2016 | Globerman et al. | |
| 9,433,407 B2 | 9/2016 | Fritzinger et al. | |
| 9,433,452 B2 | 9/2016 | Weiner et al. | |
| 9,468,479 B2 * | 10/2016 | Marotta | A61B 17/8014 |
| 9,480,512 B2 | 11/2016 | Orbay | |
| 9,486,262 B2 | 11/2016 | Andermahr et al. | |
| 9,492,213 B2 | 11/2016 | Orbay | |
| 9,510,878 B2 | 12/2016 | Nanavati et al. | |
| 9,510,880 B2 | 12/2016 | Terrill et al. | |
| 9,526,543 B2 | 12/2016 | Castaneda et al. | |
| 9,545,277 B2 | 1/2017 | Wolf et al. | |
| 9,566,097 B2 | 2/2017 | Fierlbeck et al. | |
| 9,636,157 B2 | 5/2017 | Medoff | |
| 9,649,141 B2 | 5/2017 | Raven, III et al. | |
| 9,668,794 B2 | 6/2017 | Kuster et al. | |
| 2002/0045901 A1 | 4/2002 | Wagner et al. | |
| 2004/0097937 A1 * | 5/2004 | Pike | A61B 17/80 606/282 |
| 2005/0107796 A1 | 5/2005 | Gerlach et al. | |
| 2005/0131413 A1 | 6/2005 | O'Driscoll et al. | |
| 2005/0187551 A1 | 8/2005 | Orbay et al. | |
| 2006/0149265 A1 | 7/2006 | James et al. | |
| 2006/0241607 A1 | 10/2006 | Myerson et al. | |
| 2007/0270849 A1 | 11/2007 | Orbay et al. | |
| 2008/0021477 A1 | 1/2008 | Strnad et al. | |
| 2008/0234749 A1 | 9/2008 | Forstein | |
| 2008/0275510 A1 | 11/2008 | Schonhardt et al. | |
| 2009/0024172 A1 | 1/2009 | Pizzicara | |
| 2009/0024173 A1 | 1/2009 | Reis, Jr. | |
| 2009/0118773 A1 | 5/2009 | James et al. | |
| 2009/0198285 A1 | 8/2009 | Raven, III | |
| 2009/0228010 A1 | 9/2009 | Gonzalez-Hernandez et al. | |
| 2009/0228047 A1 | 9/2009 | Derouet et al. | |
| 2009/0248084 A1 | 10/2009 | Hintermann | |
| 2009/0281543 A1 | 11/2009 | Orbay et al. | |
| 2009/0312760 A1 | 12/2009 | Forstein et al. | |
| 2010/0057086 A1 | 3/2010 | Price et al. | |
| 2010/0114097 A1 | 5/2010 | Siravo et al. | |
| 2010/0121326 A1 | 5/2010 | Woll et al. | |
| 2010/0274247 A1 | 10/2010 | Grady, Jr. et al. | |
| 2011/0106086 A1 | 5/2011 | Laird | |
| 2011/0218580 A1 | 9/2011 | Schwager et al. | |
| 2012/0059424 A1 * | 3/2012 | Epperly | A61B 17/8061 606/281 |
| 2012/0323284 A1 | 12/2012 | Baker et al. | |
| 2013/0018426 A1 | 1/2013 | Tsai et al. | |
| 2013/0060291 A1 | 3/2013 | Petersheim | |
| 2013/0123841 A1 | 5/2013 | Lyon | |
| 2013/0138156 A1 | 5/2013 | Derouet | |
| 2013/0150902 A1 | 6/2013 | Leite | |
| 2013/0165981 A1 | 6/2013 | Clasbrummet et al. | |
| 2013/0211463 A1 | 8/2013 | Mizuno et al. | |
| 2014/0005728 A1 | 1/2014 | Koay et al. | |
| 2014/0018862 A1 | 1/2014 | Koay et al. | |
| 2014/0031879 A1 | 1/2014 | Sixto, Jr. et al. | |
| 2014/0094856 A1 | 4/2014 | Sinha | |
| 2014/0121710 A1 | 5/2014 | Weaver et al. | |
| 2014/0180345 A1 | 6/2014 | Chan et al. | |
| 2014/0277178 A1 | 9/2014 | O'Kane et al. | |
| 2014/0277181 A1 | 9/2014 | Garlock | |
| 2014/0316473 A1 | 10/2014 | Pfeffer et al. | |
| 2014/0330320 A1 | 11/2014 | Wolter | |
| 2014/0371798 A1 * | 12/2014 | Platt | A61B 17/80 606/281 |
| 2014/0378975 A1 | 12/2014 | Castaneda et al. | |
| 2015/0051650 A1 | 2/2015 | Verstreken et al. | |
| 2015/0051651 A1 | 2/2015 | Terrill et al. | |
| 2015/0073486 A1 * | 3/2015 | Marotta | A61B 17/8014 606/281 |
| 2015/0105829 A1 | 4/2015 | Laird | |
| 2015/0112355 A1 | 4/2015 | Dahners et al. | |
| 2015/0134011 A1 | 5/2015 | Medoff | |
| 2015/0142065 A1 | 5/2015 | Schonhardt et al. | |
| 2015/0190185 A1 | 7/2015 | Koay et al. | |
| 2015/0209091 A1 * | 7/2015 | Sixto, Jr. | A61B 17/8057 606/289 |
| 2015/0216571 A1 | 8/2015 | Impellizzeri | |
| 2015/0223852 A1 | 8/2015 | Lietz et al. | |
| 2015/0272638 A1 | 10/2015 | Langford | |
| 2015/0282851 A1 | 10/2015 | Michel | |
| 2015/0313653 A1 | 11/2015 | Ponce et al. | |
| 2015/0313654 A1 | 11/2015 | Horan et al. | |
| 2015/0327898 A1 | 11/2015 | Martin | |
| 2015/0351816 A1 | 12/2015 | Lewis et al. | |
| 2016/0022336 A1 | 1/2016 | Bateman | |
| 2016/0030035 A1 | 2/2016 | Zajac et al. | |
| 2016/0045237 A1 | 2/2016 | Cerynik et al. | |
| 2016/0045238 A1 | 2/2016 | Bohay et al. | |
| 2016/0074081 A1 | 3/2016 | Weaver et al. | |
| 2016/0166297 A1 | 6/2016 | Mighell et al. | |
| 2016/0166298 A1 | 6/2016 | Mighell et al. | |
| 2016/0262814 A1 | 9/2016 | Wainscott | |
| 2016/0278828 A1 | 9/2016 | Ragghianti | |
| 2016/0310183 A1 | 10/2016 | Shah et al. | |
| 2016/0310185 A1 * | 10/2016 | Sixto | A61B 17/808 |
| 2016/0324552 A1 | 11/2016 | Baker et al. | |
| 2016/0354122 A1 | 12/2016 | Montello et al. | |
| 2017/0035478 A1 * | 2/2017 | Andermahr | A61B 17/8057 |
| 2017/0042592 A1 | 2/2017 | Kim | |
| 2017/0042596 A9 | 2/2017 | Mighell et al. | |
| 2017/0049493 A1 | 2/2017 | Gauneau et al. | |
| 2017/0065312 A1 | 3/2017 | Lauf et al. | |
| 2017/0215931 A1 | 8/2017 | Cremer et al. | |
| 2018/0049782 A1 * | 2/2018 | Gahman | A61B 17/80 |
| 2018/0049785 A1 * | 2/2018 | Langdale | A61B 17/8042 |
| 2018/0161081 A1 * | 6/2018 | Anding | A61B 17/80 |
| 2018/0256224 A1 * | 9/2018 | Govey | A61B 17/8014 |
| 2018/0256226 A1 * | 9/2018 | Govey | A61B 17/8061 |
| 2018/0310972 A1 * | 11/2018 | Anding | A61B 17/8014 |
| 2019/0269443 A1 * | 9/2019 | Laird, Jr. | A61B 17/8061 |
| 2019/0269446 A1 * | 9/2019 | Laird, Jr. | A61B 17/8057 |

FOREIGN PATENT DOCUMENTS

| | | |
|---|---|---|
| CN | 202821574 U | 3/2013 |
| CN | 202821575 U | 3/2013 |
| CN | 203506858 U | 4/2014 |
| CN | 203815563 U | 9/2014 |
| CN | 105982727 A | 10/2016 |
| FR | 2846870 A1 | 5/2004 |
| FR | 2928259 A1 | 9/2009 |
| FR | 3003749 A1 | 10/2014 |
| JP | 2003210478 A | 7/2003 |
| TW | 201316942 A | 5/2013 |
| WO | 2016079504 A1 | 5/2016 |

* cited by examiner

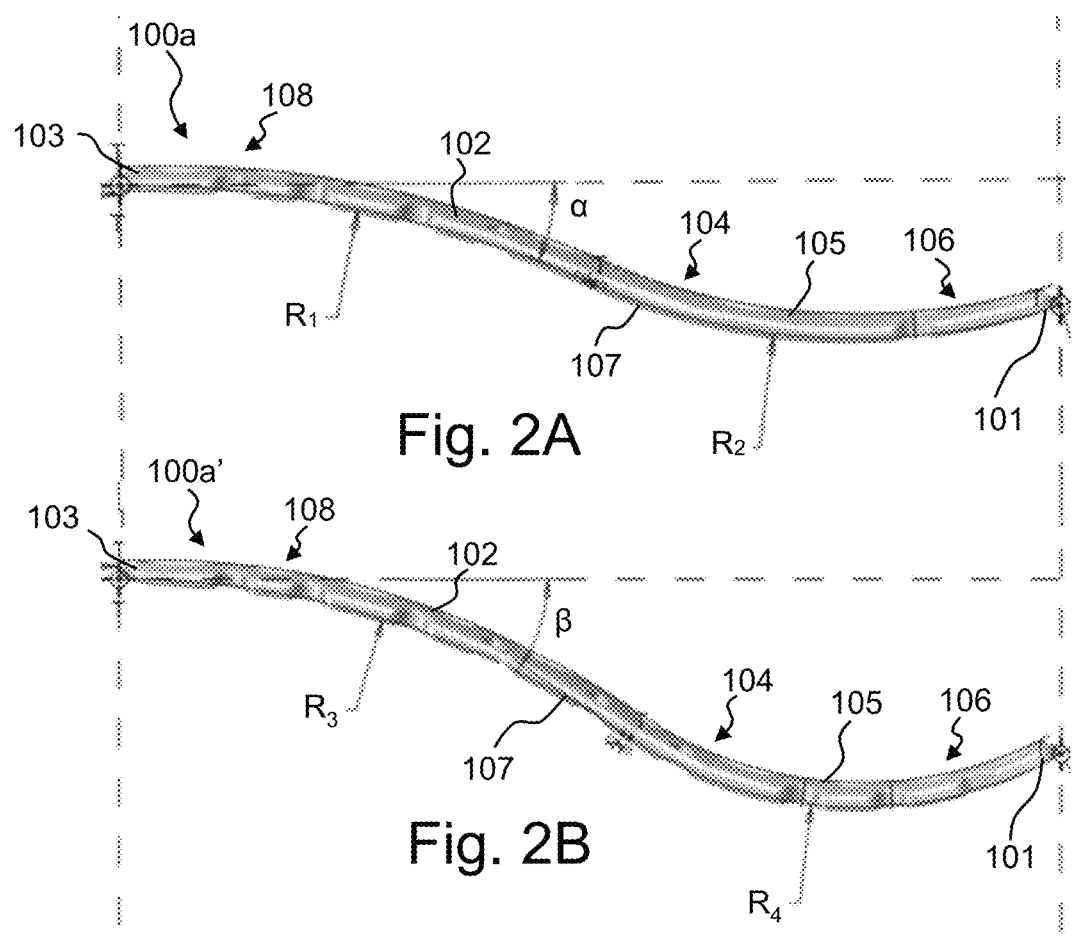

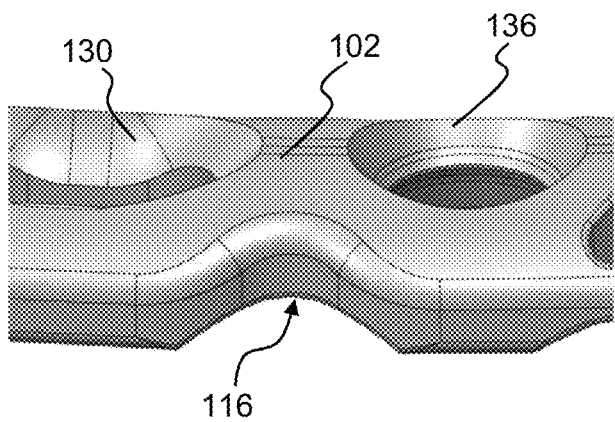
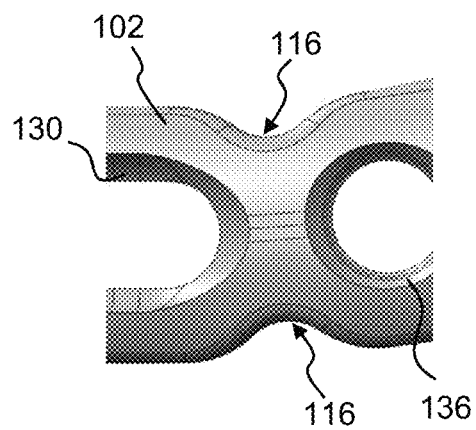
Fig. 12     Fig. 13
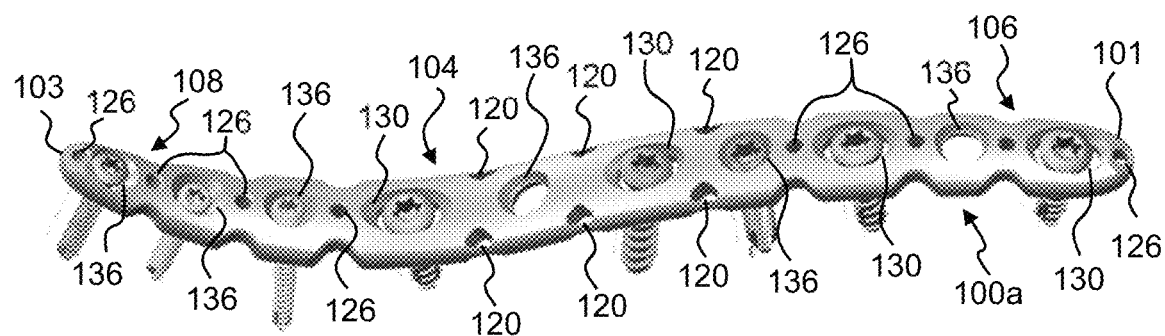
Fig. 14A
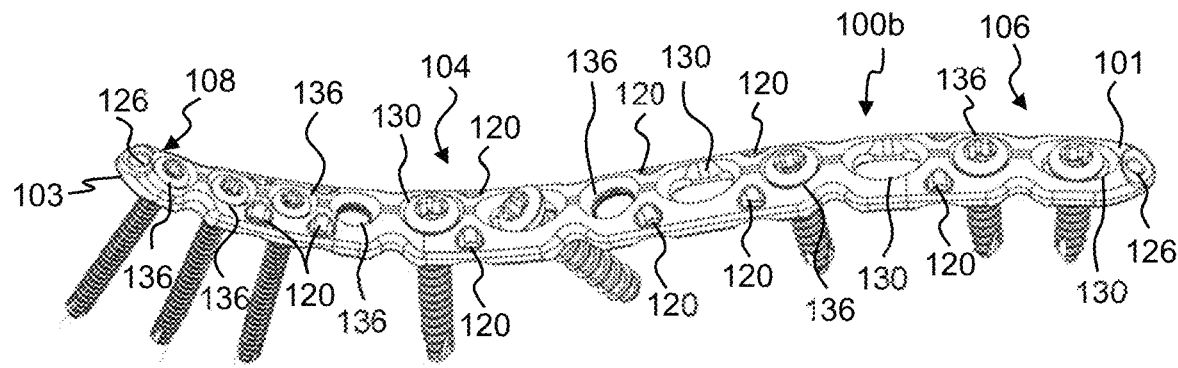
Fig. 14B

CLAVICLE FIXATION SYSTEM

CROSS REFERENCE TO RELATED APPLICATION

This application is a continuation-in-part of U.S. application Ser. No. 15/719,633, filed Sep. 29, 2017, which claims priority to U.S. provisional application No. 62/469,813, filed Mar. 10, 2017, each of which is incorporated by reference herein in its entirety for all purposes.

FIELD OF THE INVENTION

The present disclosure is generally directed to surgical devices and methods. More particularly, the present disclosure is directed to trauma plates, fasteners, intramedullary nails, systems, and methods designed to fix fractures, nonunions, and ligamentous injuries of the clavicle or the like.

BACKGROUND

The clavicle or collar bone is one of the most commonly broken bones in the body. While some clavicle fractures heal with nonoperative management, more recent studies have found that in cases of specific fracture patterns and locations, not all clavicle fractures behave the same way.

The focus of treatment of middle third fractures remains nonoperative, although evidence is mounting in support of operative treatment for displaced midshaft clavicle fractures. The incidence of nonunion of displaced distal third fractures is high, and current recommendations are to fix these injuries surgically.

Patients with the following injuries, for example, are often considered for operative intervention: complete fracture displacement, severe displacement causing tenting of the skin with the risk of puncture, fractures with significant shortening, comminuted fractures with a displaced transverse zed fragment, fractures with neurovascular compromise, displaced medial clavicular fractures with mediastinal structures at risk, polytrauma with multiple fractures, open fractures, fractures where the patient has an inability to tolerate closed treatment, fractures with interposed muscle, established symptomatic nonunion, or concomitant glenoid neck fracture.

Additionally, evidence is mounting in support of operative treatment for displaced midshaft clavicle fractures, finding that operative repair for these injuries provided better results than did nonoperative treatment. In several studies, outcomes with regard to the rate of successful bone union, functional outcome, time required for patients to resume their daily activities, and overall patient satisfaction were superior in the operative group than in nonoperative patients. There was also significantly less posttraumatic clavicular shortening in the surgical group.

With an increased consideration of operative repair, improved clavicle fixation systems are desired.

SUMMARY

Clavicle bone plates, intramedullary clavicle nails, systems, and methods of treatment are provided. The systems and devices may be particularly suitable for fixation of the clavicle. Although generally described with reference to the clavicle, it will be appreciated that the systems and devices may be adapted for use with any long bone, short bone, flat bone, or the like.

In at least one embodiment, the present disclosure provides clavicle fixation device includes an elongated plate extending between first and second ends and defining a central portion, a first end portion between the central portion and the first end, and a second end portion between the central portion and the second end. The elongated plate defines a plurality of spaced apart screw holes. At least one pair of relief cuts extends into the elongated plate on opposite sides thereof and are axially positioned between a pair of the spaced apart screw holes. At least one pair of suture holes extends into the elongated plate along opposite sides thereof and are axially positioned between a pair of the spaced apart screw holes.

In at least one embodiment, the present disclosure provides a clavicle fixation device including an elongated plate extending between first and second ends, the elongated plate defining a plurality of spaced apart screw holes. At least one pair of relief cuts extends into the elongated plate on opposite sides thereof, the at least one pair of relief cuts axially positioned between a pair of the spaced apart screw holes and at least one pair of suture holes along opposite sides of the elongated plate, the at least one pair of suture holes axially positioned between a pair of the spaced apart screw holes. At least one pair of relief cuts is axially aligned with a pair of suture holes to define combined holes on opposite sides of the elongated plate.

In at least one embodiment, the present disclosure provides a method of preparing a clavicle fixation device which comprises an elongated plate extending between first and second ends, the elongated plate defining a plurality of spaced apart screw holes, wherein at least one pair of relief cuts extends into the elongated plate on opposite sides thereof, the at least one pair of relief cuts axially positioned between a pair of the spaced apart screw holes and at least one pair of suture holes along opposite sides of the elongated plate, the at least one pair of suture holes axially positioned between a pair of the spaced apart screw holes; and wherein at least one pair of relief cuts is axially aligned with a pair of suture holes to define combined holes on opposite sides of the elongated plate. The method includes the step of bending the elongated plate in the anterior/posterior direction and/or in the caudal/cranial direction at at least one combined hole pair such that the elongated plate has a contour which complements the contour of a clavicle anterior or superior surface.

Also provided are methods of treatment and kits including bone plates and/or intramedullary nails of varying shapes and sizes, bone anchors, fasteners, insertion tools, and other components for installing the same.

BRIEF DESCRIPTION OF THE DRAWINGS

The accompanying drawings, which are included to provide a further understanding of the present disclosure, are incorporated in and constitute a part of this specification, illustrate aspects of the present disclosure and together with the detailed description serve to explain the principles of the present disclosure. No attempt is made to show structural details of the present disclosure in more detail than may be necessary for a fundamental understanding of the present disclosure and the various ways in which it may be practiced. In the drawings:

FIGS. 2A-2D are side elevation views of anterior fixation plates in accordance with embodiments of the disclosure illustrating different contours;

FIG. 12 is a side perspective view of a portion of an anterior fixation plate in accordance with an embodiment of the disclosure illustrating the side relief cuts thereof;

FIG. 13 is a plan view illustrating the side relief cuts of FIG. 12;

FIGS. 14A and 14B are perspective views of the anterior lateral fixation plates of FIGS. 1A and 1B, respectively;

FIG. 21 F is a side elevation view and perspective view of a superior fixation plate in accordance with an embodiment of the disclosure illustrating different contours;

DETAILED DESCRIPTION

Figure 1A:
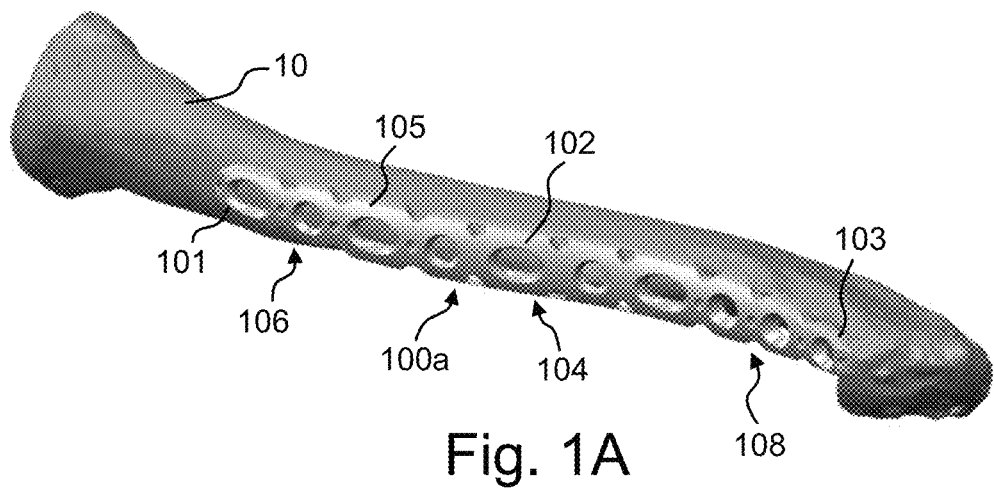
FIGS. 1A and 1B are perspective views of anterior fixation plates in accordance with embodiments of the present disclosure, each shown positioned along a clavicle.

The aspects of the present disclosure and the various features and advantageous details thereof are explained more fully with reference to the non-limiting aspects and examples that are described and/or illustrated in the accompanying drawings and detailed in the following description. It should be noted that the features illustrated in the drawings are not necessarily drawn to scale, and features of one aspect may be employed with other aspects as the skilled artisan would recognize, even if not explicitly stated herein. Descriptions of well-known components and processing techniques may be omitted so as to not unnecessarily obscure the aspects of the present disclosure. The examples used herein are intended merely to facilitate an understanding of ways in which the present disclosure may be practiced and to further enable those of skill in the art to practice the aspects of the present disclosure. Accordingly, the examples and aspects herein should not be construed as limiting the scope of the present disclosure, which is defined solely by the appended claims and applicable law. Moreover, it is noted that like reference numerals represent similar parts throughout the several views of the drawings.

Orthopedic bone plates, intramedullary nails, systems, and methods of treatment are provided. The bone plates and nails may be useful in repair of the clavicle. Although further described with reference to treatment of the clavicle, it will be appreciated that the system and devices may be adapted for use with any bones, including but not limited to, the femur, tibia, humerus, fibula, ulna, radius, bones of the foot, bones of the hand, or the like.

Referring to FIGS. 1-19, anterior fixation plates 100a-100d in accordance with various embodiments of the disclosure will be described. FIGS. 1a, 1b, 3a, 3b, 4a and 4b illustrate anterior fixation plates 100a, 100b positioned along an anterior surface of a clavicle 10. Each anterior fixation plate 100a, 100b includes an elongate body 102 extending between opposed ends 101, 103 with an outer surface 105 and an inner, bone contacting surface 107.

Figure 2C:
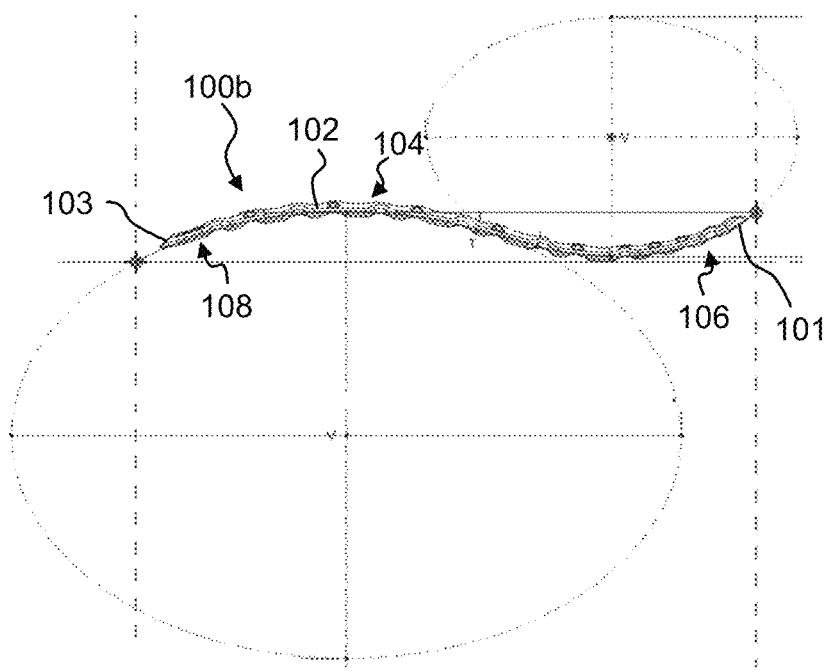
Figure 2D:
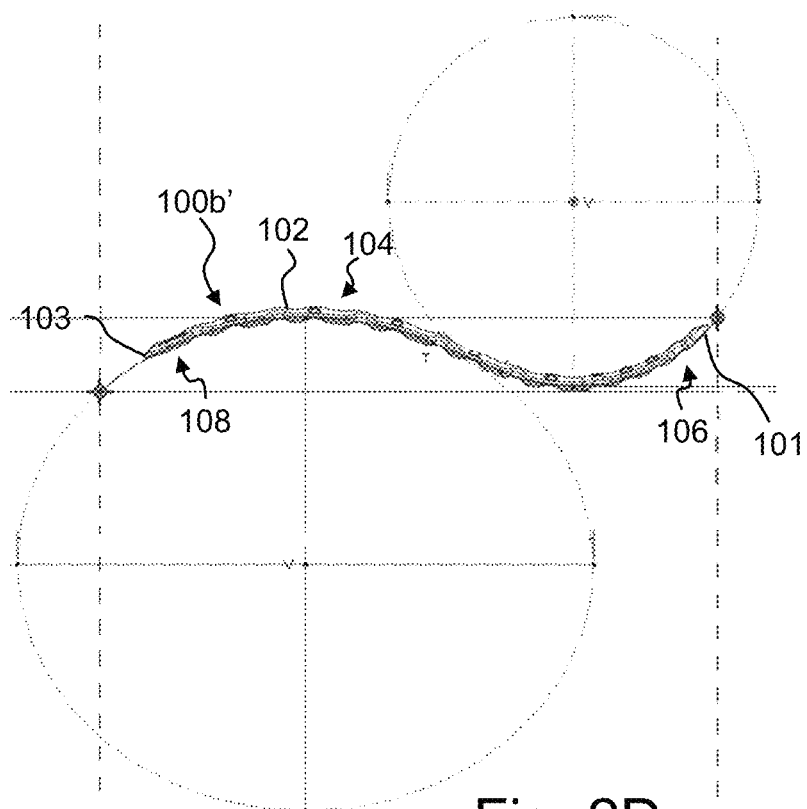
Figure 3A:
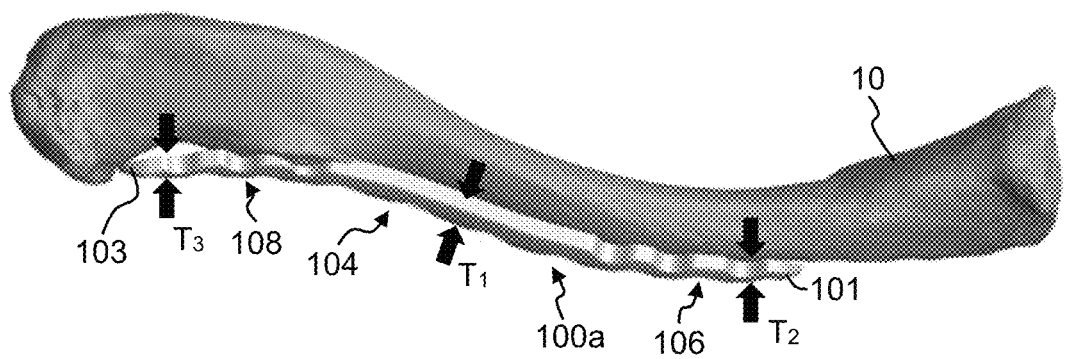
FIGS. 3A and 3B are top plan views of the anterior fixation plates of FIGS. 1A and 1B, respectively.
Figure 3B:
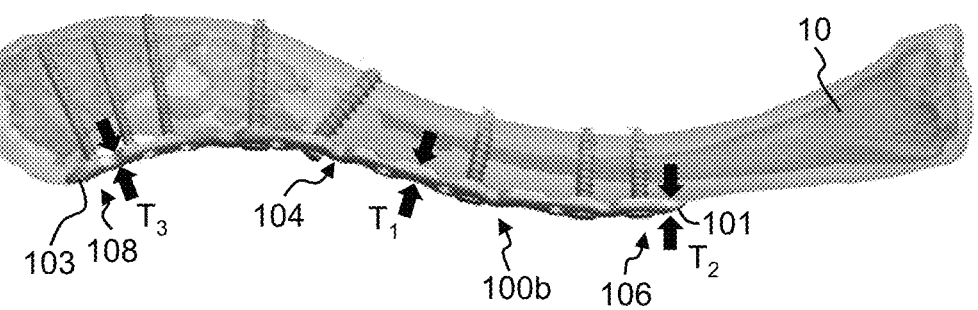

Referring to FIGS. 2A-2D, the anterior plates 100a, 100a', 100b, 100b' are anatomically contoured to fit along the curved anatomy of the anterior clavicle. The anterior plates 100a, 100a', 100b, 100b' are interchangeable for left-side and right-side clavicles. As the curvature of the bone varies between individuals, the anterior plates 100a, 100a', 100b, 100b' are offered in multiple contours, with exemplary contours illustrated in FIGS. 2A-2D. Each plate 100a, 100a', 100b, 100b' includes a central portion 104 extending between end portions 106, 108. Referring first to FIGS. 2A and 2B, the contour of the plate 100a, 100a' is defined by the angle $\alpha$, $\beta$ of the end portions 106, 108 relative to the central portion 104 as well as the curvature $R_1$, $R_2$, $R_3$, $R_4$ of each end portion 106, 108. The angle $\alpha$ of plate 100a may range, for example, from about 20-30°, about 20-25°, about 23-25°, or about 24°. The angle $\beta$ of plate 100' may range, for example, from about 30-40°, about 30-35°, about 33-35°, or about 34°. The radius may range, for example, from about 100-200 mm, about 120-160 mm, or about 140 mm. The radius $R_2$ may range, for example, from about 10-100 mm, about 60-100 mm, or about 80 mm. The radius $R_3$ may range, for example, from about 50-150 mm, about 90-130 mm, or about 110 mm. The radius $R_4$ may range, for example, from about 10-100 mm, about 30-70 mm, or about 50 mm. In the illustrated embodiments, the angle $\alpha$ of plate 100 (for example 24°) is smaller than the angle $\beta$ of plate 100' (for example 34°) and the radiuses $R_1$, $R_2$ (for example 140 mm, 80 mm) are larger than the radiuses $R_3$, $R_4$ (for example 110 mm, 50 mm). With the illustrated configurations, the plate 100a of FIG. 2A is said to have a shallow configuration while the plate 100a' of FIG. 2B is said to have a deep configuration. Referring to FIGS. 2C and 2D, the plates 100b, 100b' have a longer length with the ends 106, 108 extending over a greater arcuate length. Each arcuate length is defined by the arc of a respective ellipse. As in the previous embodiments, the plates 100b, 100b' may have varying radiuses to achieve a shallow configuration as in plate 100b or a deep configuration as in plate 100b'. The plates 100a, 100a', 100b, 100b' may have various angles and radiuses or elliptical dimensions and are not limited to the illustrative examples. Selecting a contoured plate 100a, 100a', 100b, 100b' closely matching the bone's contour minimizes plate prominence and irritation under soft tissue.

Figure 4A:
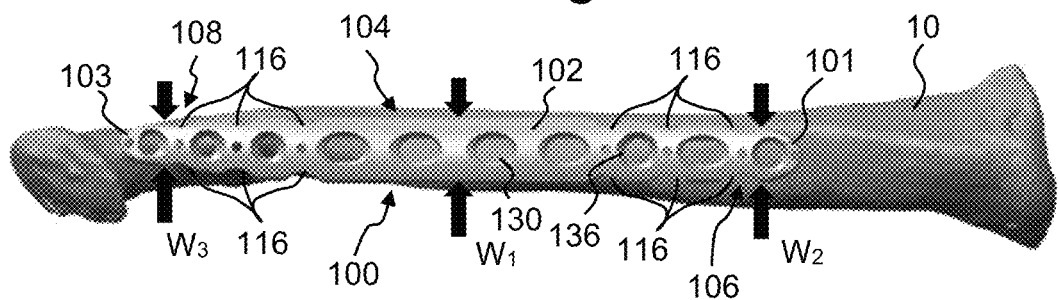
FIGS. 4A and 4B are front elevation views of the anterior fixation plates of FIGS. 1A and 1B, respectively.
Figure 4B:
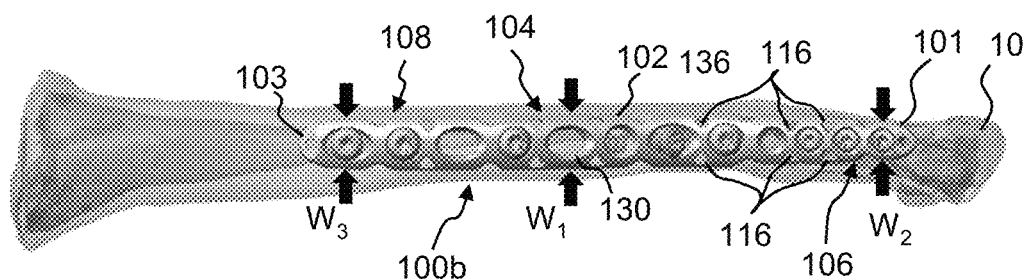
Figure 5A:
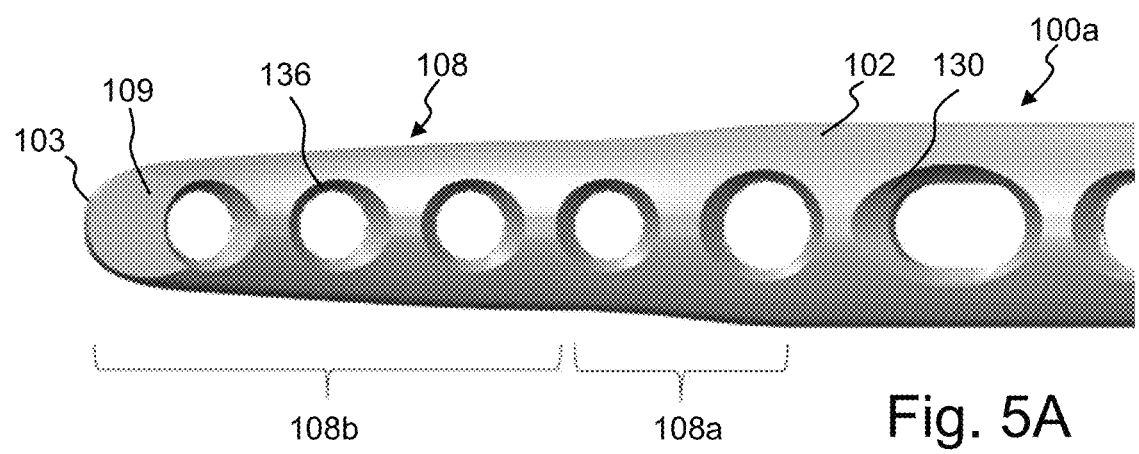
FIGS. 5A and 5B are plan views of end portions of anterior fixation plates in accordance with embodiments of the disclosure.
Figure 5B:
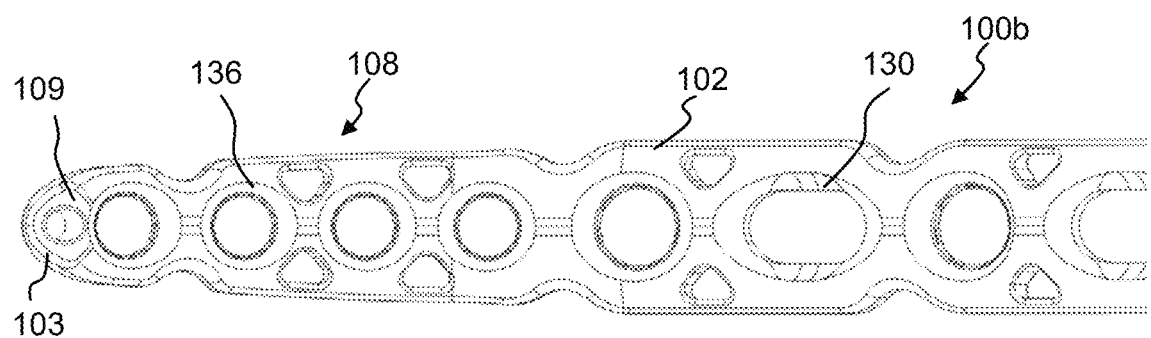
Figure 6:
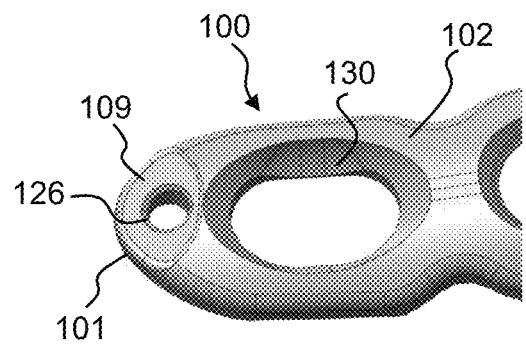
FIG. 6 is a perspective view of an end tip of an anterior fixation plate in accordance with an embodiment of the disclosure.
Figure 7:
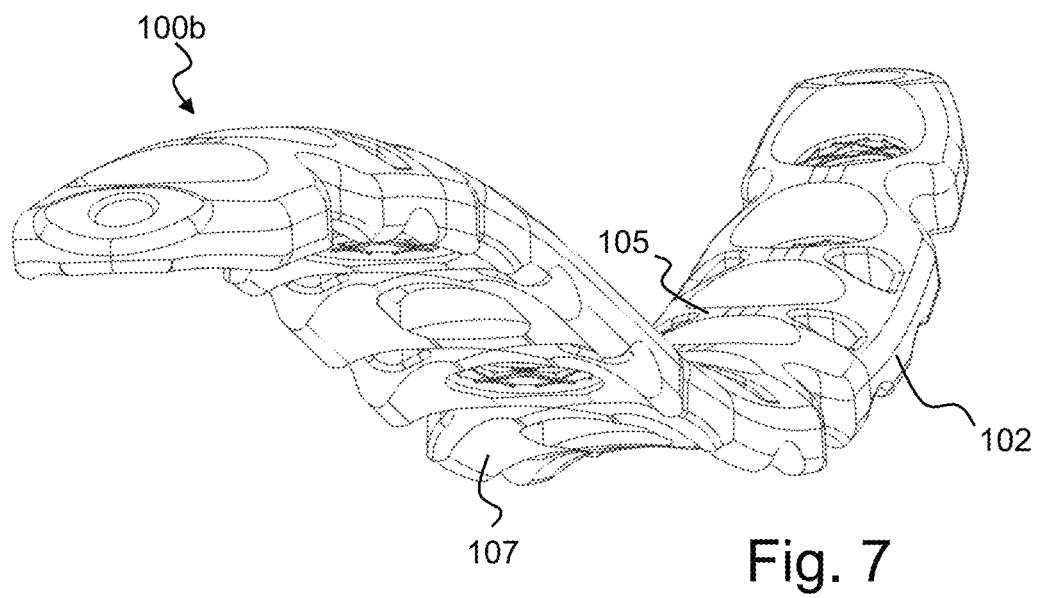
FIG. 7 is a perspective view of an anterior fixation plate in accordance with an embodiment of the disclosure illustrating the rounded top and undersides thereof.
Figure 8:
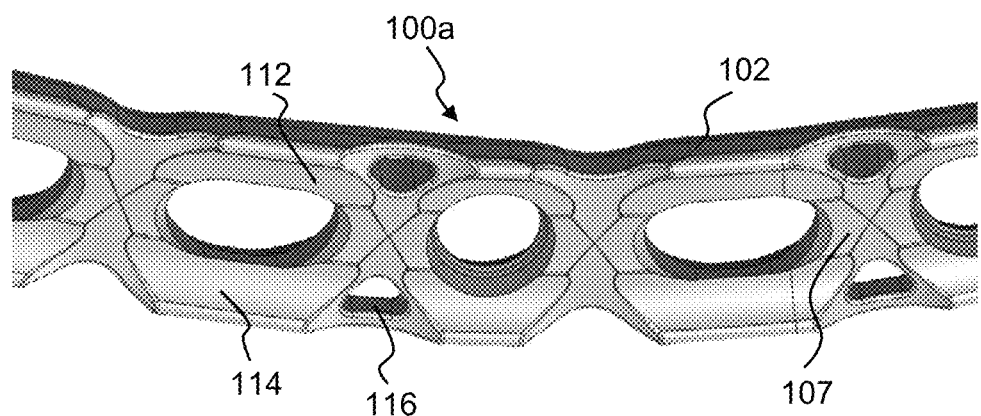
FIG. 8 is a perspective view of the underside of a central portion of an anterior fixation plate in accordance with an embodiment of the disclosure.
Figure 9:
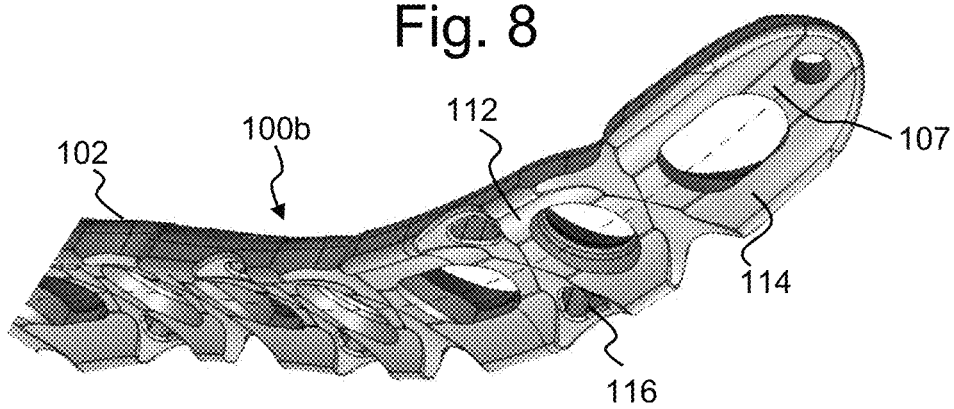
FIG. 9 is a perspective view of the underside of an end portion of the anterior fixation plate of FIG. 8.

Referring to FIGS. 3A-6, the anterior fixation plate 100a, 100b is further contoured in both width and cross-sectional thickness. In the illustrated embodiment, the plate 100a, 100b has a largest cross-sectional thickness $T_1$ in the central portion 104 and then tapers to smaller cross-sectional thickness $T_2$, $T_3$ in each end portion 106, 108. The thicknesses $T_2$, $T_3$ in the end portions 106, 108 may be the same or distinct from one another. As illustrated in FIGS. 5A, 5B and 6, the plate 100a, 100b may include additional taper 109 at the plate ends 101, 103, beyond the last hole. The additional taper 109 aids sub-muscular insertion of the plate for minimally-invasive procedures.

The plate 100a, 100b also has a largest width $W_1$ in the central portion 104 and then narrows to smaller widths $W_2$, $W_3$ in each end portion 106, 108. The widths $W_2$, $W_3$ in the end portions 106, 108 may be the same or distinct from one another. Referring to FIG. 5A, in the plate 100a, the end portion 108 narrows at different rates, with the portion 108a closest to the central portion 104 narrowing more steeply than the portion 108b toward the end 103, which has a more gradual narrowing. Referring to FIG. 5B, in the plate 100b, the end portion 108 narrows at a constant rate.

Figure 40A:
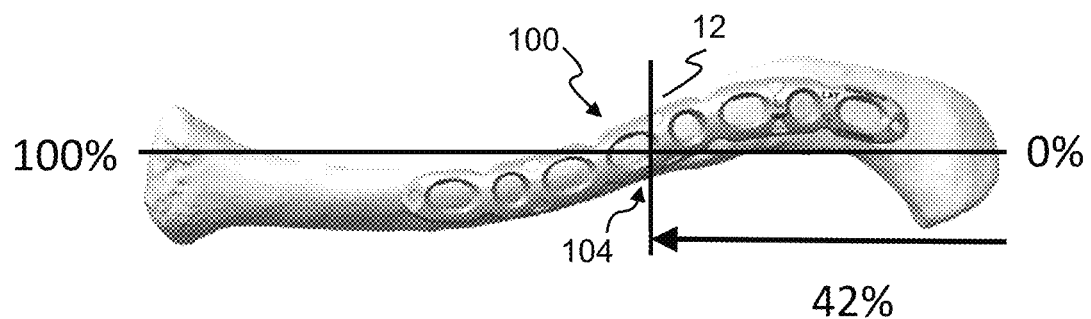
FIGS. 40A, 40B, 40C, 40D and 40E illustrated the position of clavicle common fracture zones and the positioning of a plate in accordance with the embodiment of the disclosure relative thereto.
Figure 40B:
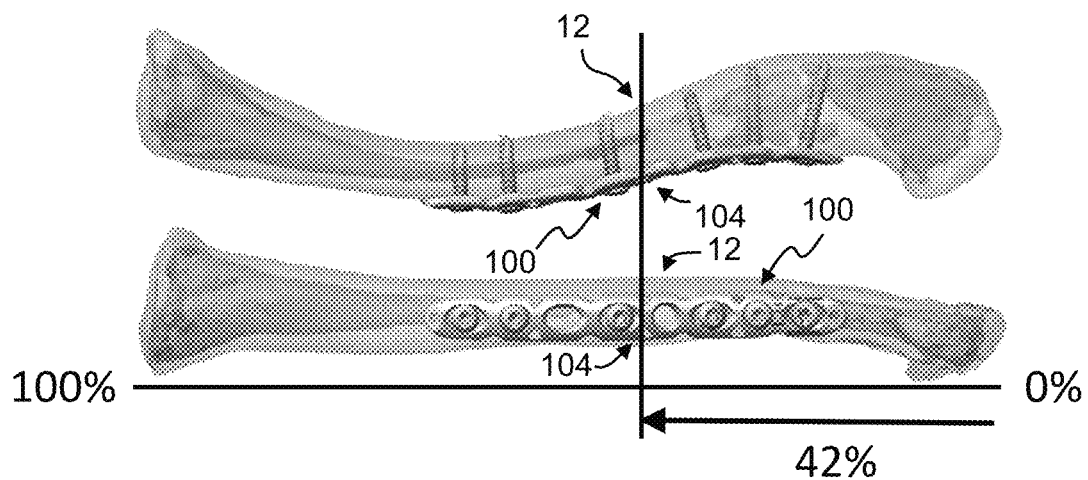
Figure 40C:
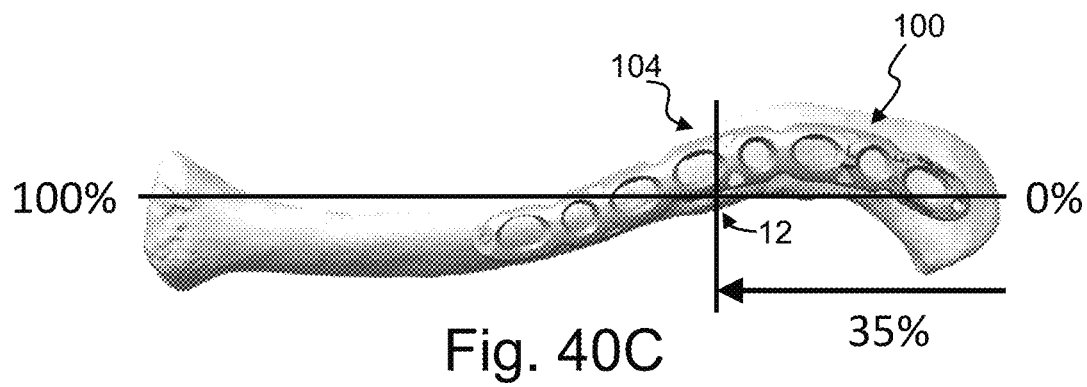
Figure 40D:
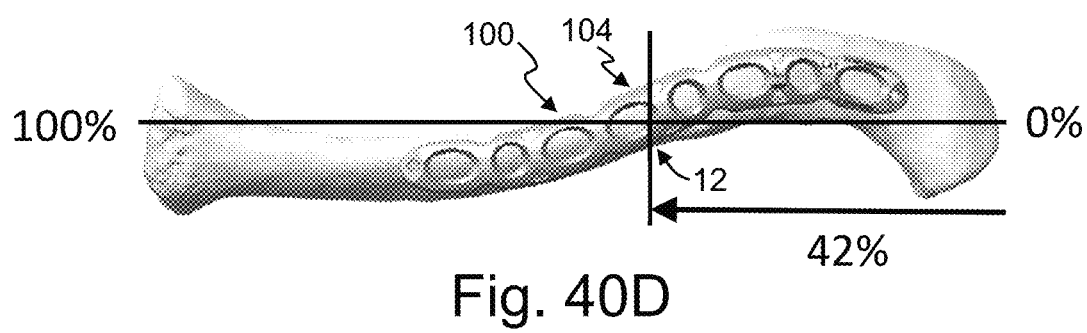
Figure 40E:
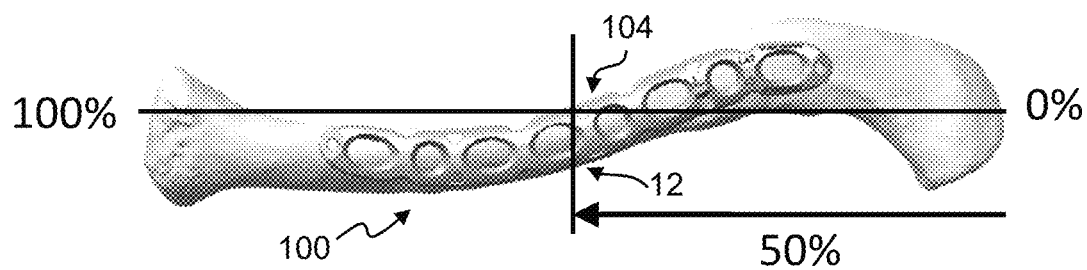
Figure 41:
FIG. 41 is a side elevation view of an intramedullary clavicle nail in accordance with an embodiment of the invention.

The plate 100a, 100b thicknesses and widths are selected such that the plate 100a, 100b optimally spans a common clavicle fracture zone. Image research study of clavicle fractures is used to identify the most common fracture zones. For example, referring to FIGS. 40A, 40B and 40D, image studies may show that a common fracture zone 12 occurs at a location which is about 42% of the length of the bone 10. Accordingly, the plates 100 are configured such that the central portion 104 will overly the area at about 42% of the length of the bone 10 when the plate 100 is attached to the bone 10. FIGS. 40C and 40E illustrate instances wherein studies show a common fracture zone 12 at different positions along the bone 10, namely, at 35% of the bone length and 50% of the bone length, respectively. Accordingly, the plates 100 are configured such that the central portion 104 will overly the area at about 35% of the length of the bone 10 or 50% of the length of the bone when the plate 100 is attached to the bone 10. The length, thicknesses and width of each plate portion 104, 106, 108 are selected such that the optimal span comprises a thicker cross-sectional area and greater moment of inertia for a distance appropriate to the extent of the fracture zone. At either end of the optimal span, where strength is less essential, the plate 100 narrows in width and tapers lower in thickness. This narrowing and taper enables the plate 100 to be low-profile, minimizing prominence and irritation under soft tissue.

Referring to FIGS. 7-11, the plate 100a, 100b may also include a rounded outer surface 105 and a rounded inner surface 107. The rounded surfaces 105, 107 assist in keeping plate prominence to a minimum. The inner surface 107 may further include cylindrical or elliptical undercuts 112, 114 sweeping the length of the plate 100. The undercuts 112, 114 reduce the contact surface of the plate 100a, 100b against the clavicle bone 10. This may reduce damage to the periosteum, preserve blood supply, reduce osteonecrosis, and speed fracture consolidation.

Figure 10:
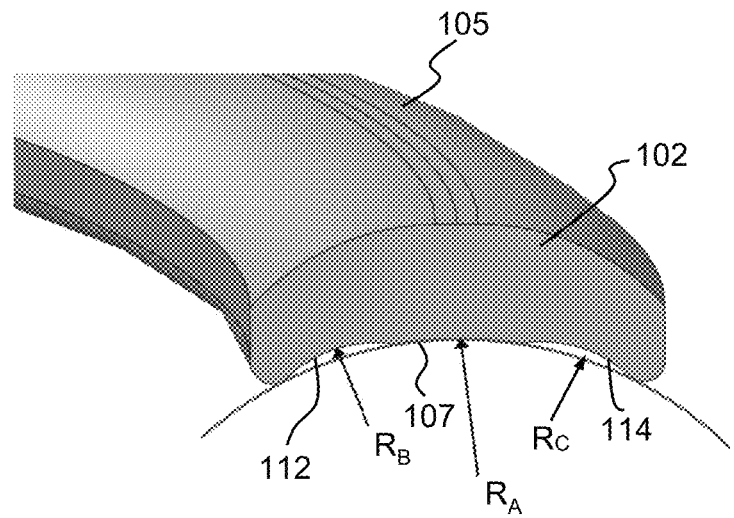
FIG. 10 is a top perspective view illustrating the cross-sectional profile of a fixation plate in accordance with an embodiment of the disclosure.
Figure 11:
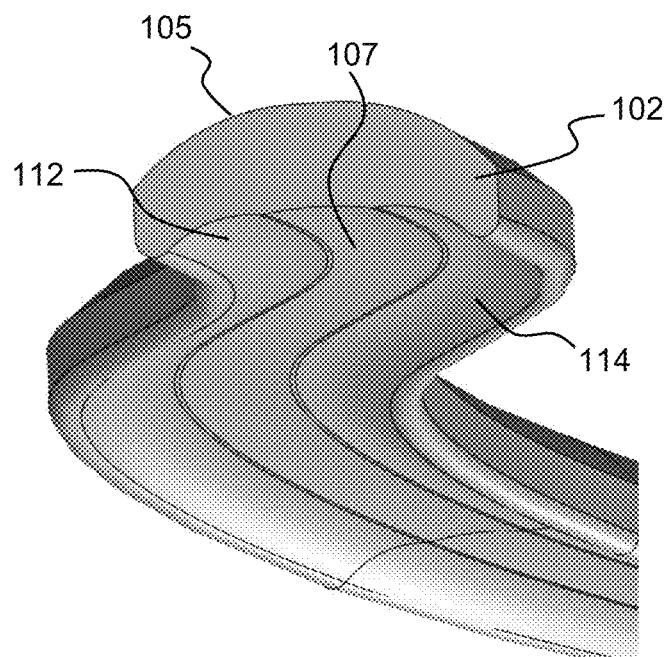
FIG. 11 is a bottom perspective view illustrating the underside of the cross-sectional profile of FIG. 10.
Figure 15A:
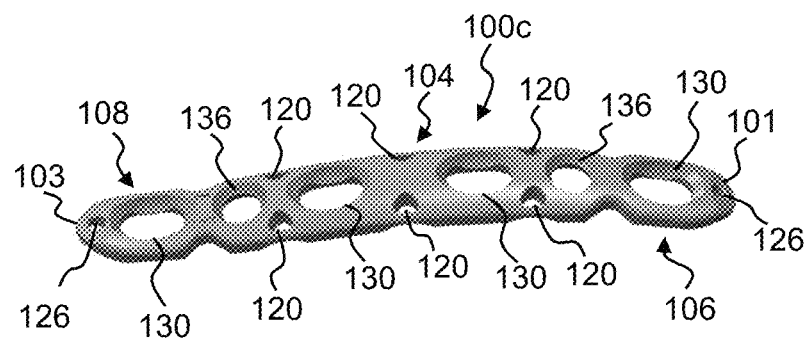
FIG. 15A is a perspective view of an anterior midshaft fixation plate in accordance with an embodiment of the disclosure.
Figure 15B:
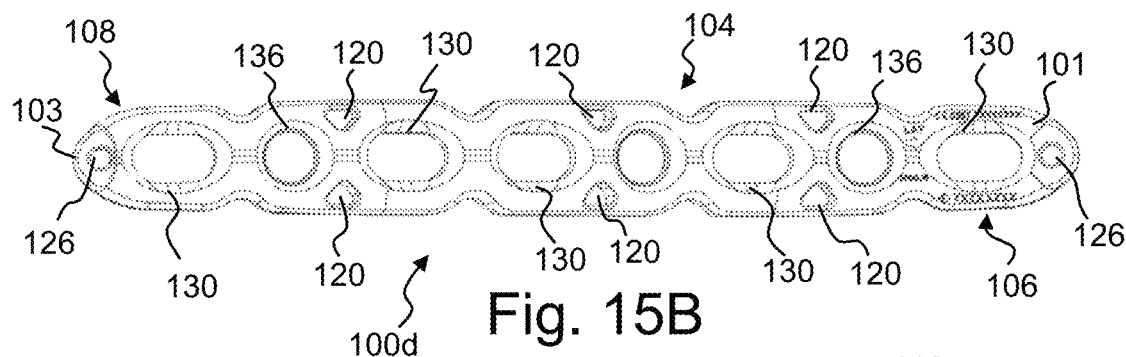
FIGS. 15B, 15C and 15D are a top plan view, side elevation view and a perspective view, respectively, of another anterior midshaft fixation plate in accordance with an embodiment of the disclosure.
Figure 15C:
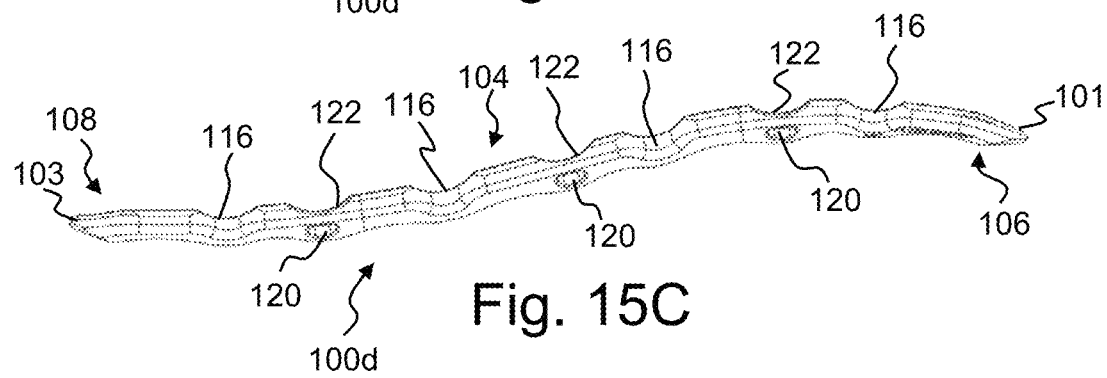
Figure 15D:
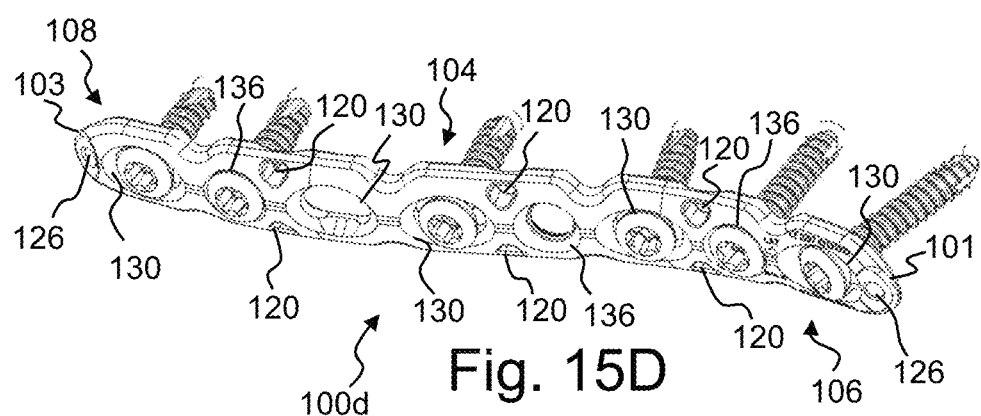

Referring to FIGS. 10 and 11, an exemplary undercut pattern is illustrated. The plate inner surface 107 has a curvature with a radius of $R_A$ and defines the bone contacting surface. The radius $R_A$ is similar to the radius of the clavicle bone surface. Each of the undercuts 112, 114 extends the length of the plate 100 and has a radius $R_B$, $R_C$, respectively. The radiuses $R_B$, $R_C$ may be the same or may be different from one another. The radiuses $R_B$, $R_C$ of the undercuts 112, 114 are smaller than the radius containing the plate/bone contact surfaces $R_A$. The undercuts 112, 114 reduce plate contact with the bone surface while only minimally reducing cross-sectional strength. While two undercuts are illustrated, more or fewer undercuts, either circular or elliptical, may be utilized.

Figure 1B:
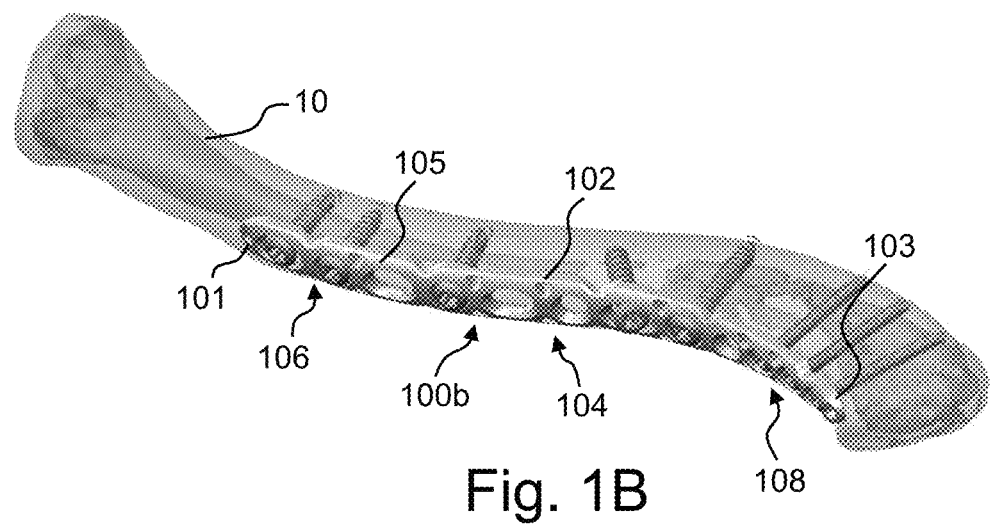

Referring to FIGS. 12 and 13, side relief cuts 116 extend into the body 102 of the plate 100a, 100b along the sides thereof. In the illustrated embodiments, the relief cuts 116 are provided in opposed pairs on each side of the body 102, however, other configurations may be utilized. The relief cuts 116 are positioned between screw holes thereby reducing the moment of inertia between the screw holes to allow preferential bending between holes, helping to minimize deformation of the screw holes. The illustrated relief cuts 116 have a rounded or smooth configuration to minimize the risk of kinking or fracture. As illustrated in FIGS. 1A, 4A and 14A, the relief cuts 116 in the plate 100a are present near the end portions 106, 108 of the plate 100a where contour customization by bending is the most likely to be desired, however, other configurations may be utilized. For example, in the plate 100b, as illustrated in FIGS. 1B, 4B and 14B, the relief cuts 116 are present in the central portion 104 as well as near the end portions 106, 108 of the plate 100b.

Referring to FIGS. 14A-19, the plates 100a-100d may be provided with various through holes, including oblong suture holes 120, round K-wire holes 126, dynamic compression plating (DCP) slots 130, and polyaxial holes 136. The oblong suture holes 120 are positioned along but inward of the side edges of the plate body 102. The round K-wire holes 126 are provided at each end 101, 103 of the plate 100, 100" and may be provided at other more central areas, as shown in FIG. 14A. The oblong suture holes 120 and the round K-wire holes 126 may be used as K-wire holes to allow provisional fixation of the plate 100, 100" with K-wires. Additionally, the oblong suture holes 120 may be used for suture and an undercut 122 is aligned with each oblong suture hole 120 and extends into the inner surface 107 of the plate 100a-100d. The undercuts 122 have a width that is wider than the width of the corresponding suture hole 120. The undercuts 122 enable free passage of suture underneath the plate 100, 100" without interference at the plate/bone interface. The undercuts 122 help reduce the moment of inertia between screw holes to allow preferential bending between holes, helping to minimize deformation of screw holes. This is useful for plate contour customization. The undercuts 122 also serve to further reduce the contact surface of the inner surface 107 of the plate 100a-100d. The undercuts 122 may be co-located with relief cuts 116 and suture holes 120.

In the illustrated embodiments, the oblong suture holes 120 have a rounded triangular configuration and are positioned between screw holes 130, 136. With this configuration, the oblong suture holes 120 reduce the moment of inertia between screw holes to allow preferential bending between holes, helping to minimize deformation of screw holes. This is useful for plate contour customization. While the oblong suture holes 120 are illustrated with a rounded triangular configuration, other configurations may be utilized, for example, elliptical, round, oval.

The oblong suture holes 120 also facilitate passage of suture/needles to serve as anchor points useful for reattachment and repositioning of soft tissue damaged during surgery which may aid post-surgical soft tissue healing. The oblong suture holes 120 also facilitate passage of suture/needles for cerclage techniques which may aid in reduction and fixation of bone fragments, particularly "butterfly" fragments on the inferior side of the bone. In the illustrated embodiment, the opposed suture holes 120 on either side of the plate 100a-100d allow for cerclage running from one side of the plate, down under the bone, up to the opposing suture hole, and potentially across again to the originating hole for successive loops. These opposing holes 120 also aid cerclage perpendicular to the plate trajectory. This is the optimal angle for applying force to reduce fragments toward the plate.

Figure 16:
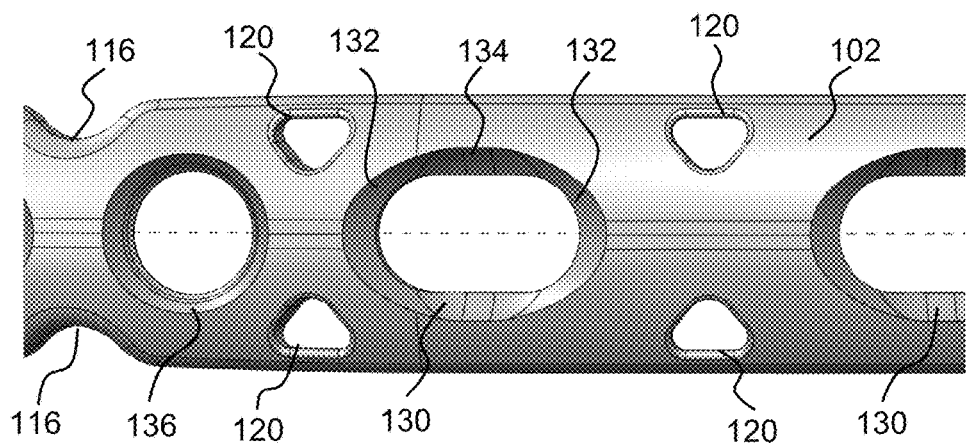
FIG. 16 is a plan view of a central portion of an anterior fixation plate in accordance with an embodiment of the disclosure.
Figure 17:
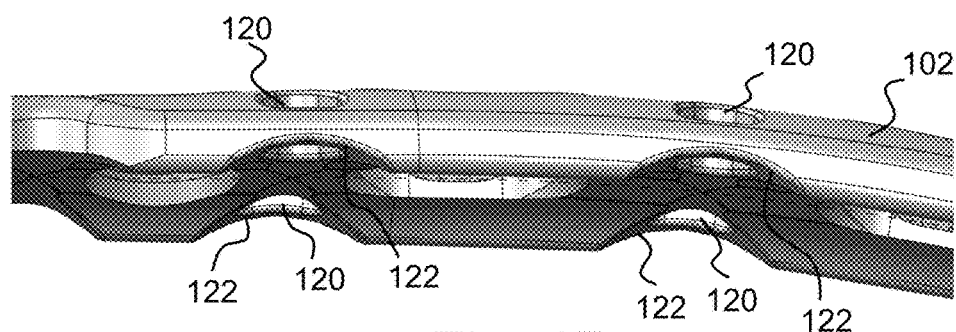
FIG. 17 is a side perspective view of the anterior fixation plate of FIG. 16.
Figure 18:
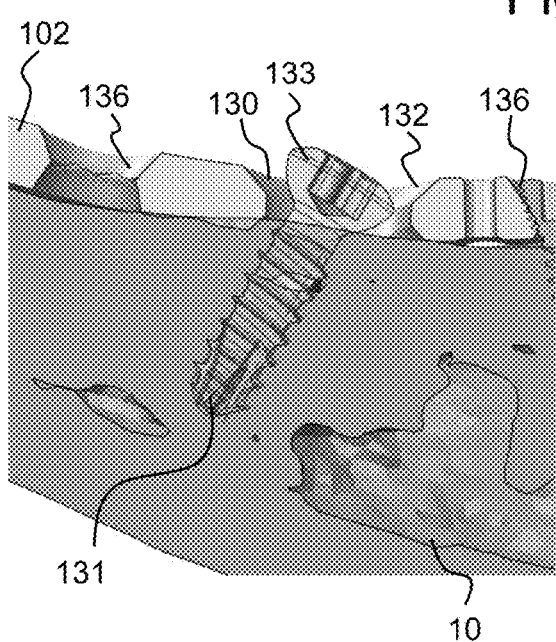
FIG. 18 is a cross-sectional view of a portion of an anterior fixation plate in accordance with an embodiment of the invention illustrating a screw extending through a dynamic compression plating slot thereof.

Referring to FIGS. 16 and 18, each DCP slot 130 has an oblong configuration with tapered end walls 132 and a central neutral head receiving area 134. Contact of a screw head 133 with the tapered end wall 132 may cause medial-lateral motion of the plate 100a-100d relative to the bone to compress a bone fracture. Standard neutral placement may also be achieved by positioning the screw head in the central neutral head receiving area 134. Compression or neutral placement is typically achieved using a non-locking screw 131, for example, a 3.5 mm non-locking screw. The DCP slot 130 also enables off-axis, or oblique, screw trajectories in the plane of the slot using non-locking screws. Cancellous screws enable oblique or neutral screw trajectories through the DCP slot 130, useful for fragment capture or load neutralization across the fracture line.

Figure 19:
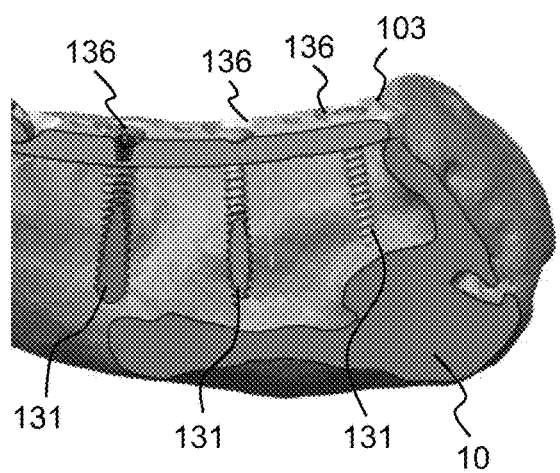
FIG. 19 is a cross-sectional view of a portion of an anterior fixation plate in accordance with an embodiment of the invention illustrating screws extending through polyaxial holes thereof.

The polyaxial holes 136 accept locking and non-locking screws, both inserted within a cone of angulation, as illustrated in FIG. 18. The polyaxial holes 136 may be configured to accept different sized screws, for example, 3.5 mm screws at the midshaft end 101 of the plate 100 and 2.5 mm screws at the far lateral end 103 of the plate 100. The nominal trajectory of the far lateral holes assists in aiming screws to good quality bone and away from the acromioclavicular joint space, as illustrated in FIG. 19.

As illustrated in FIGS. 14A-15C, the DCP slots 130 and polyaxial holes 136 may be arranged in various configurations. In the anterior lateral plate 100a illustrated in FIG. 14A, the DCP slots 130 and the polyaxial holes 136 alternate in the central portion 104 and the end portion 106 while the end portion 108 includes consecutive polyaxial holes 136. The anterior lateral plate 100b illustrated in FIG. 14B is similar to the plate 100a wherein the DCP slots 130 and the polyaxial holes 136 alternate in the central portion 104 and the end portion 106 while the end portion 108 includes consecutive polyaxial holes 136, however the end portion 108 includes additional polyaxial holes 136 compared to the previous embodiment. In the anterior midshaft plate 100c illustrated in FIG. 15A, the DCP slots 130 and the polyaxial holes 136 alternate over the length of the plate 100c. In the anterior midshaft plate 100d illustrated in FIGS. 15B-15D, the DCP slots 130 and the polyaxial holes 136 generally alternate over the length of the plate 100d with the exception of an additional DCP slot near the end 108. Other configurations other than those illustrated may also be utilized.

Figure 20A:
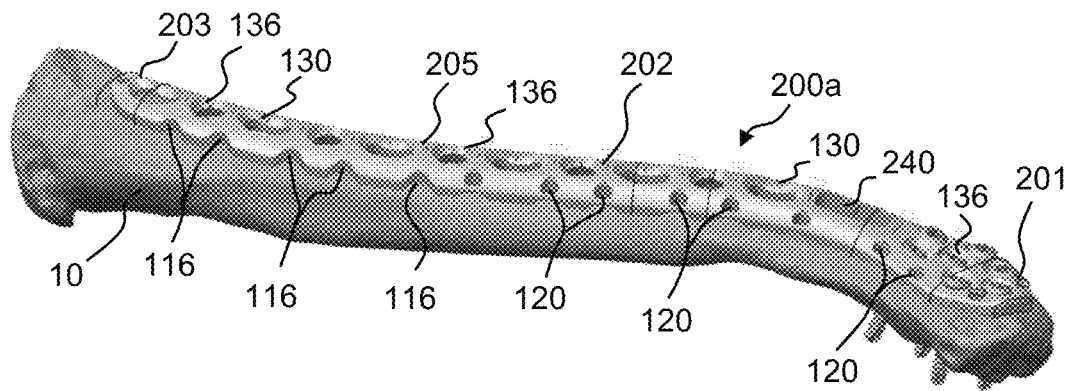
FIGS. 20A, 20B and 20C are perspective views of superior fixation plates in accordance with embodiments of the present disclosure, each shown positioned along a clavicle.
Figure 20B:
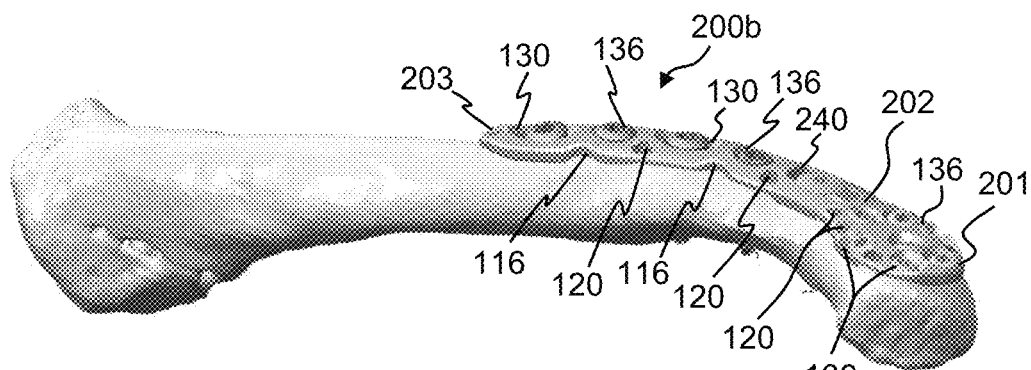
Figure 20C:
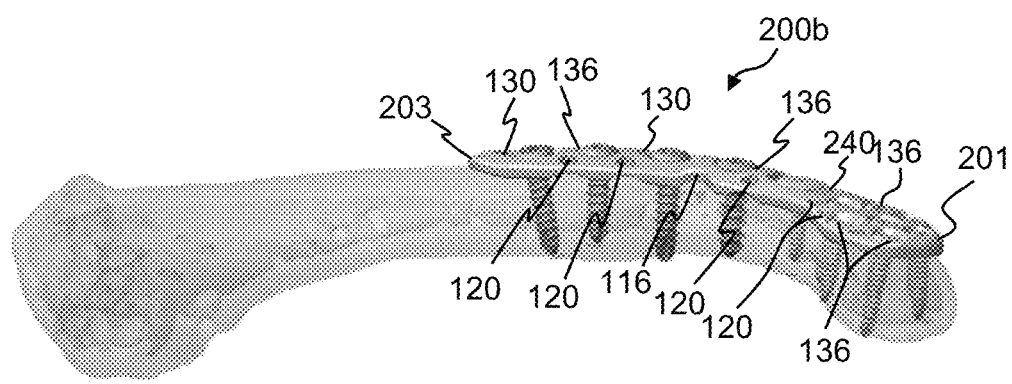
Figure 21A:
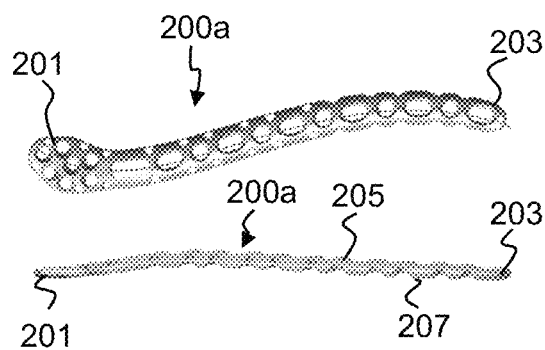
FIGS. 21A and 21B are top and side elevation views of superior fixation plates in accordance with an embodiments of the disclosure illustrating different contours.
Figure 21B:
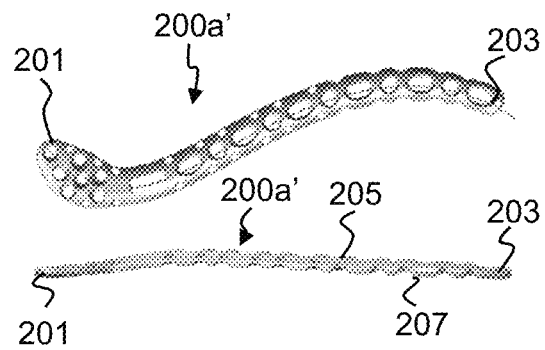
Figure 21C:
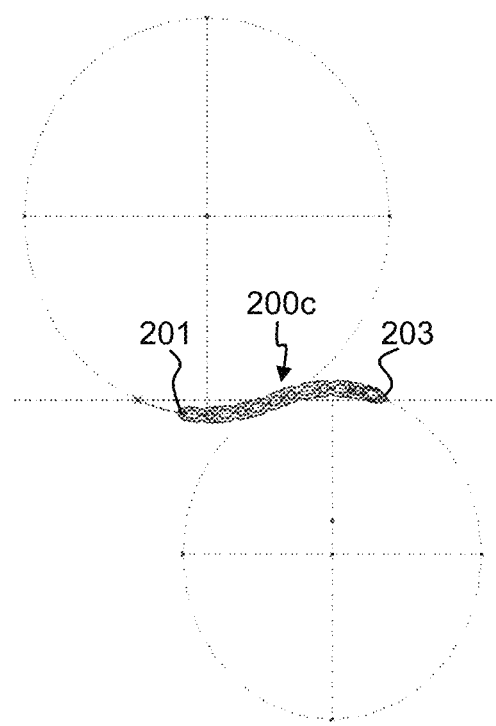
FIGS. 21C, 21D and 21 E are top views of superior fixation plates in accordance with an embodiments of the disclosure illustrating additional contours.
Figure 21D:
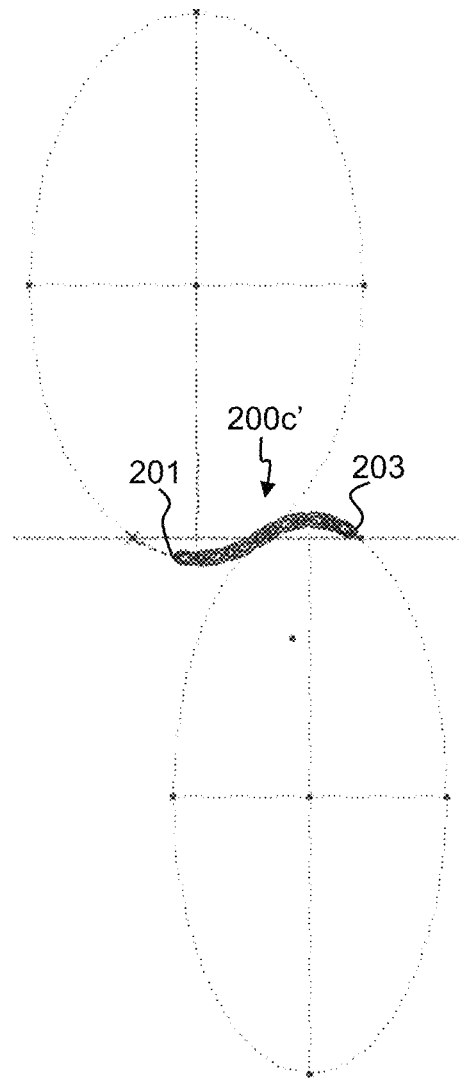
Figure 21E:
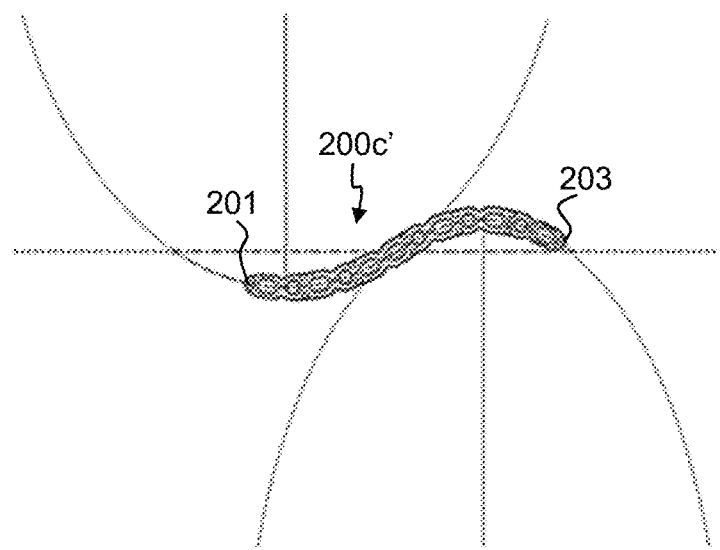
Figure 21F:
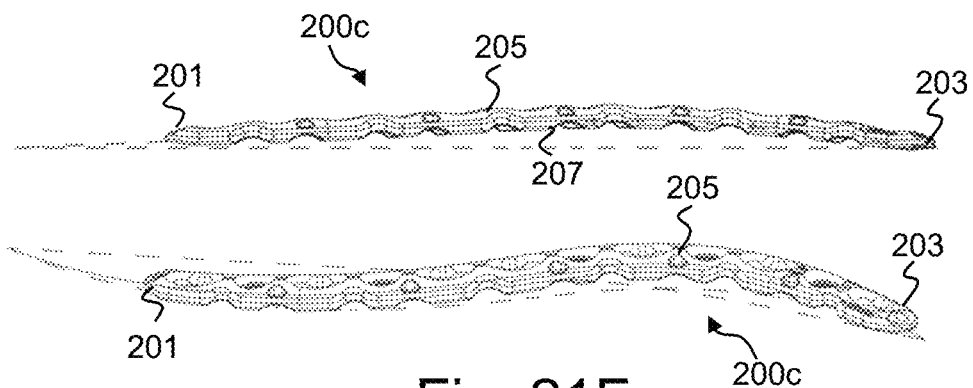

Referring to FIGS. 20A-28B, superior fixation plates 200a-200d in accordance with various embodiments of the disclosure will be described. FIGS. 20A-20C illustrate superior fixation plates 200a, 200b positioned along a superior surface of a respective clavicle 10. The superior fixation plates 200a-200d are similar to the anterior fixation plates described above and each includes an elongate body 202 extending between opposed ends 201, 203 with an outer surface 205 and an inner, bone contacting surface 207. The superior fixation plates 200a-200d may include any of the features described with respect to the anterior plates, including rounded outer and inner surfaces 205, 207, undercuts 112, 114 on the inner surface 207, side relief cuts 116, oblong suture holes 120, undercuts 122, round K-wire holes 126, DCP slots 130 and polyaxial holes 136.

Referring to FIGS. 21A-21F, the superior plates 200a-200c are anatomically contoured to fit along the curved anatomy of the superior clavicle. The superior plates 200a-200c are not interchangeable for left-side and right-side clavicles, but instead are configured for either the left-side or right-side clavicle. As the curvature of the bone varies between individuals, the superior plates 200a-200c are offered in multiple contours, with exemplary contours illustrated in FIGS. 21A-21F. Each plate 200a-200c' has an "S" curvature in the A/P direction and a slight bow in the caudal/cranial direction. Plates 200a-200c' following contours with less (FIG. 21A and FIG. 21C) or more (FIG. 21B or FIG. 21D) "S" curvature may be referred to as "shallow" or "deep" contoured plates, respectively. As illustrated, the plates 200a-200c' may have various angles and radiuses or elliptical dimensions, however, the configurations are not limited to the illustrative examples. Selecting a contoured plate 200a-200c' closely matching the bone's contour minimizes plate prominence and irritation under soft tissue.

Figure 22:
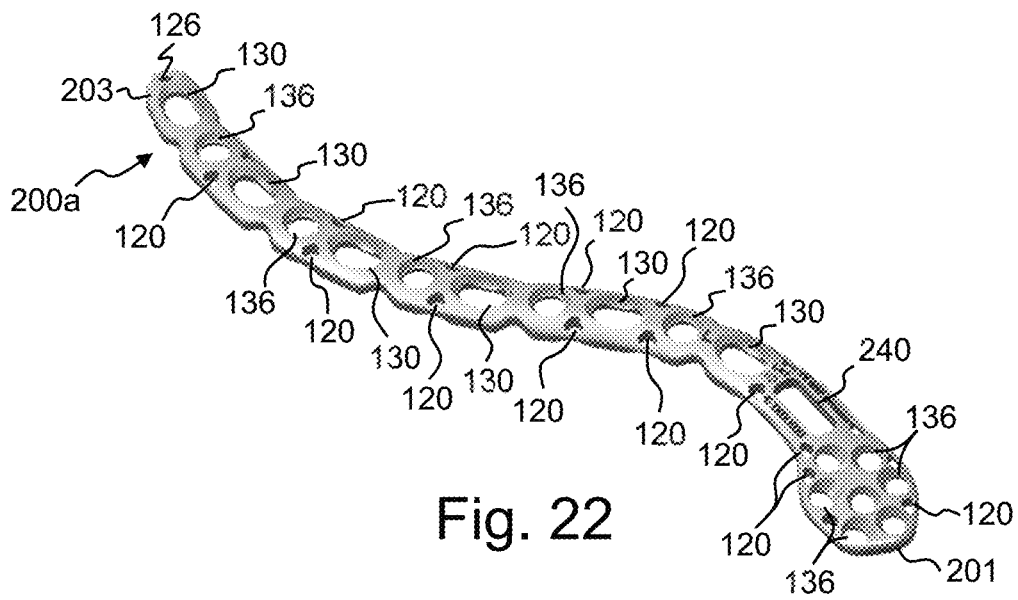
FIG. 22 is a perspective of the superior fixation plate of FIG. 20.
Figure 23:
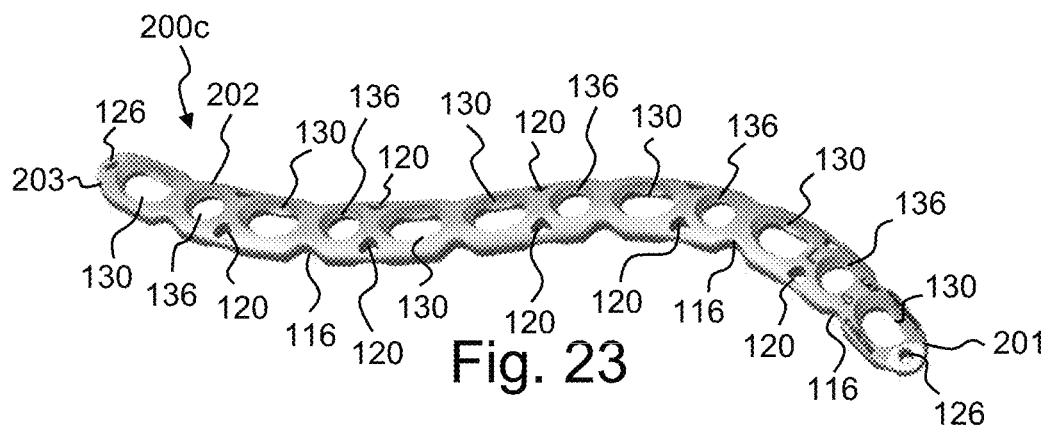
FIG. 23 is a perspective view of another superior fixation plate in accordance with an embodiment of the present disclosure.
Figure 24A:
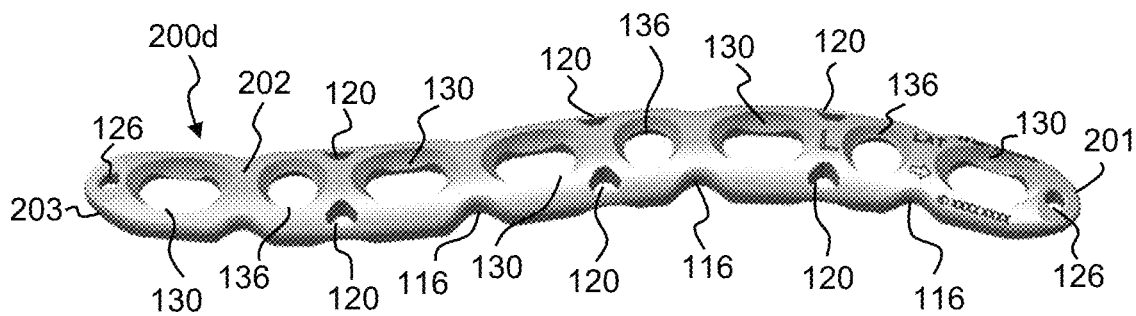
FIGS. 24A, 24B and 24C are a perspective view, a top view, and a bottom perspective view of another superior fixation plate in accordance with an embodiment of the present disclosure.
Figure 24B:
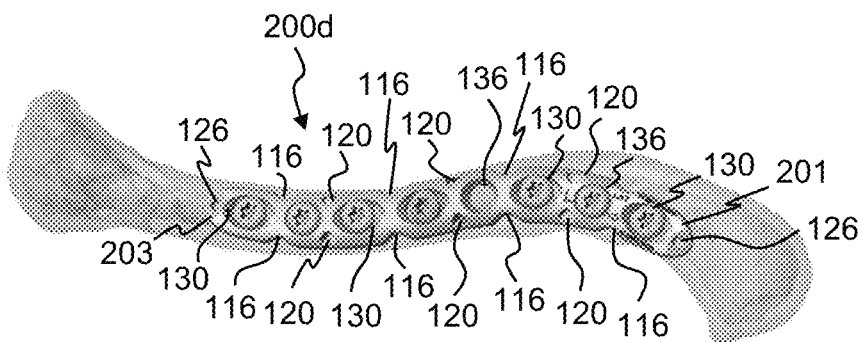
Figure 24C:
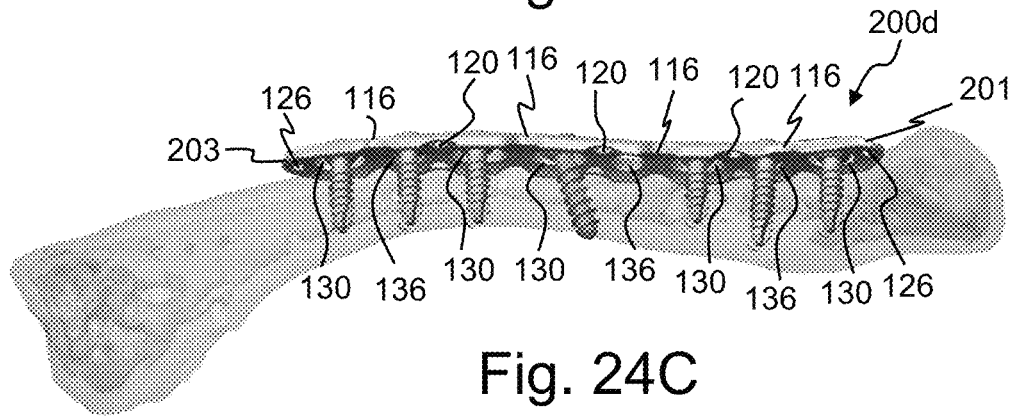
Figure 25A:
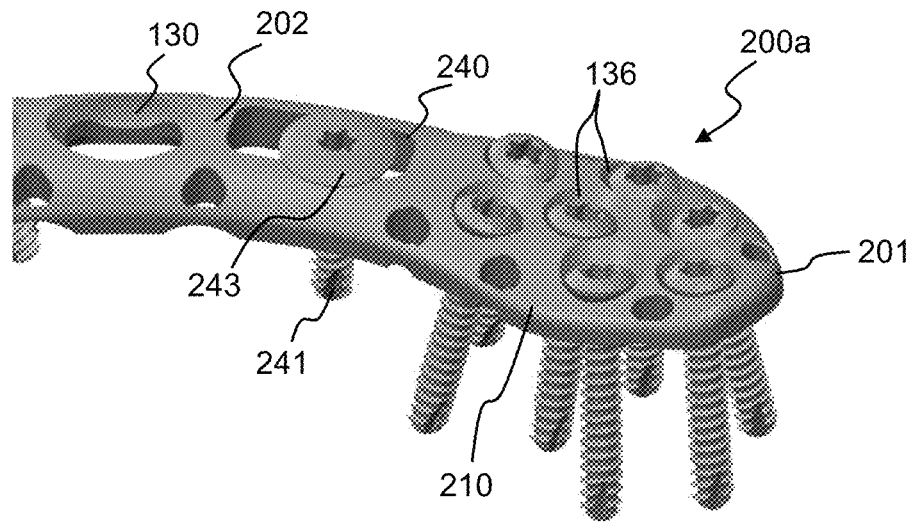
FIGS. 25A, 25B, 26A and 26B are top and side perspective views, respectively, of end portions of superior fixation plates in accordance with embodiments of the disclosure illustrating a plurality of screws extending through the polyaxial holes thereof.
Figure 25B:
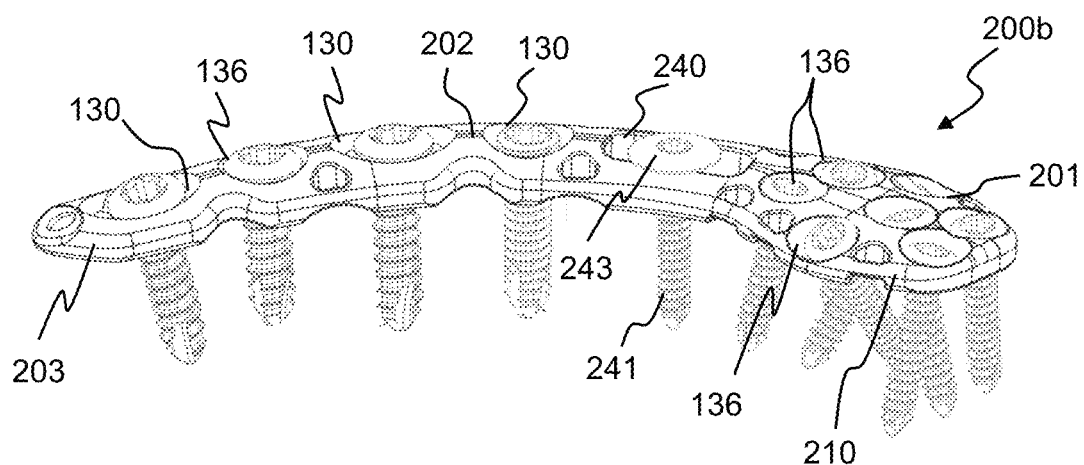
Figure 26A:
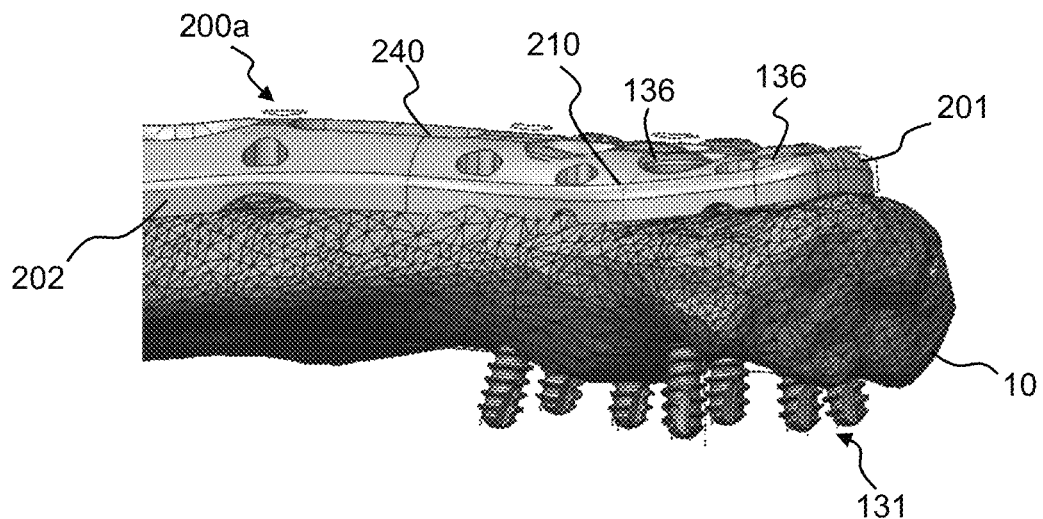
Figure 26B:
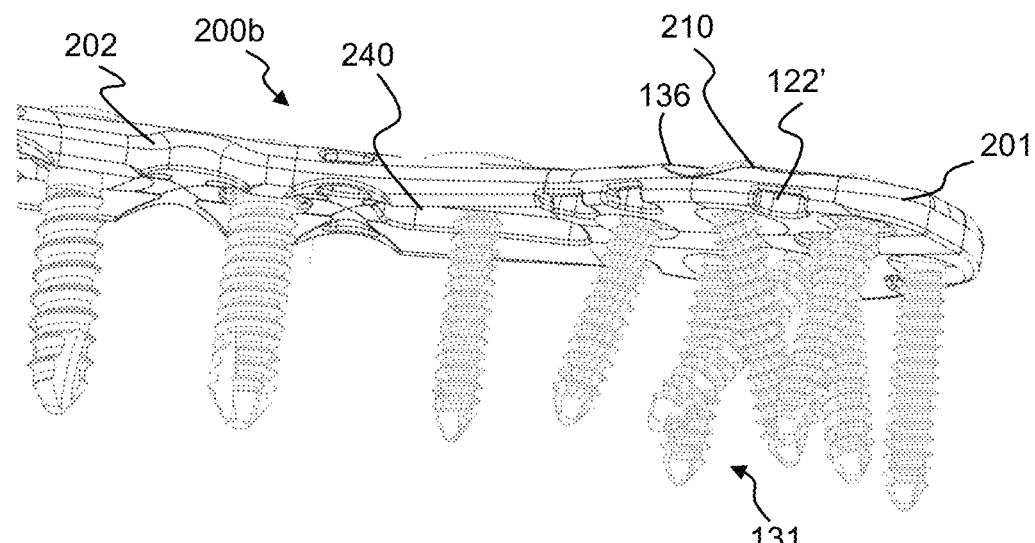
Figure 27A:
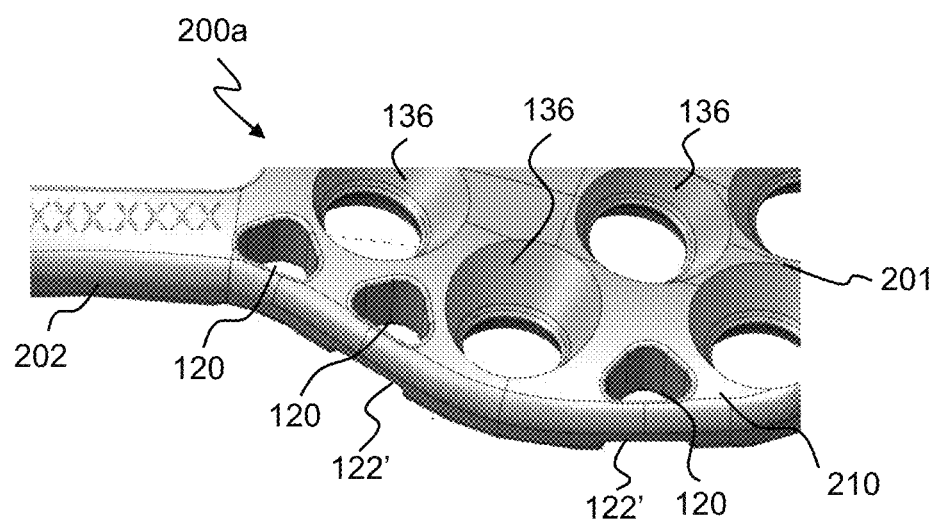
FIGS. 27A, 27B, 28A and 28B are top and bottom perspective views of a portion of the end of superior fixation plates in accordance with embodiments of the disclosure illustrating the k-wire/suture holes thereof.
Figure 27B:
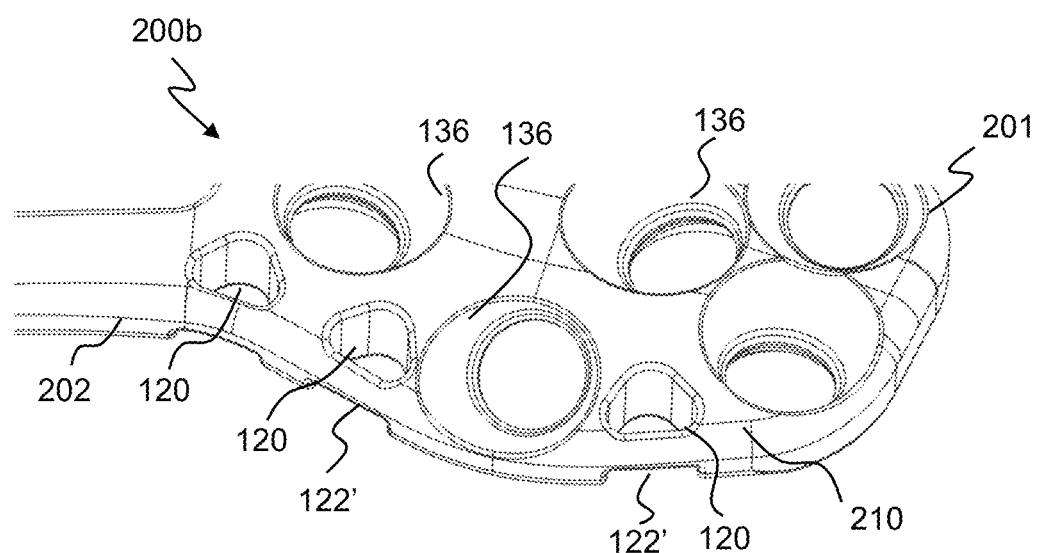
Figure 28A:
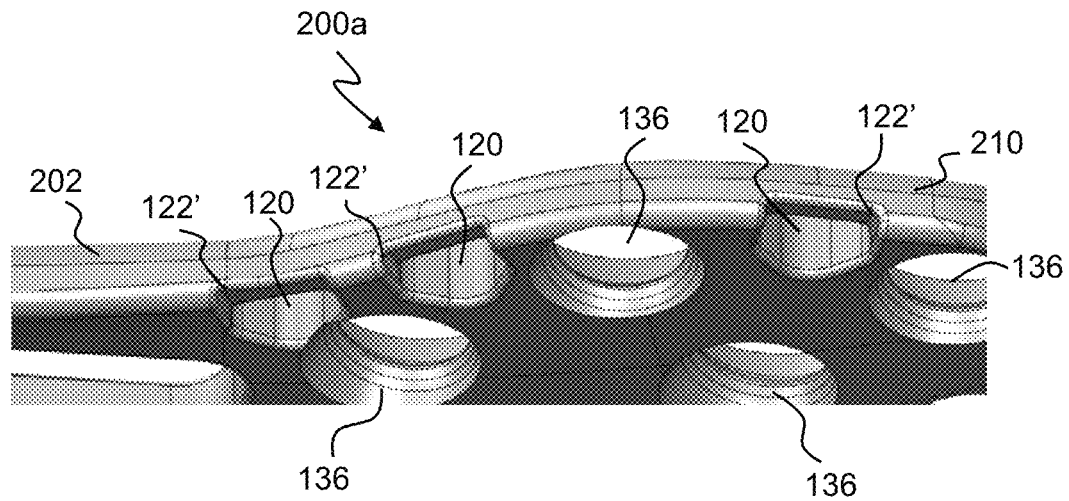
Figure 28B:
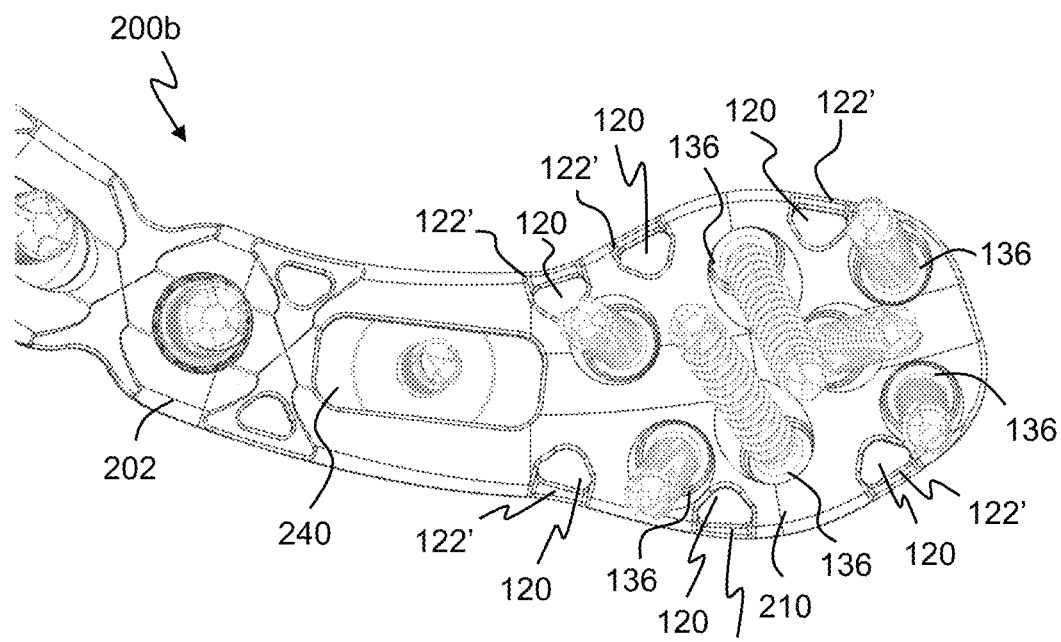
Figure 29:
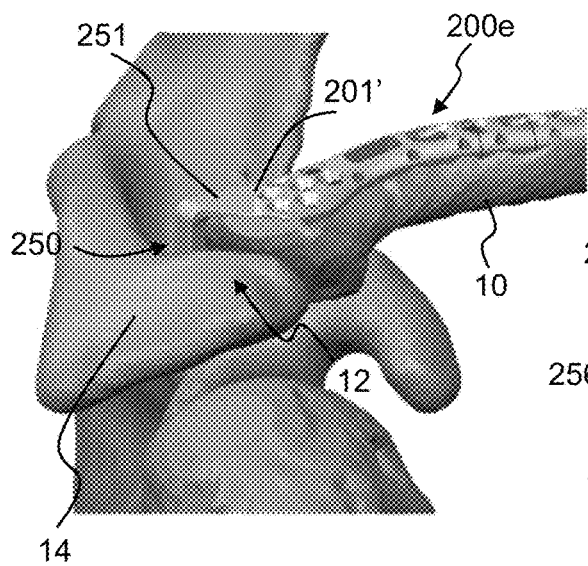
FIGS. 29 and 30 are front perspective views of a hook plate in accordance with an embodiment of the disclosure positioned relative a clavicle and AC joint, with FIG. 30 illustrating the clavicle and AC joint transparently.
Figure 30:
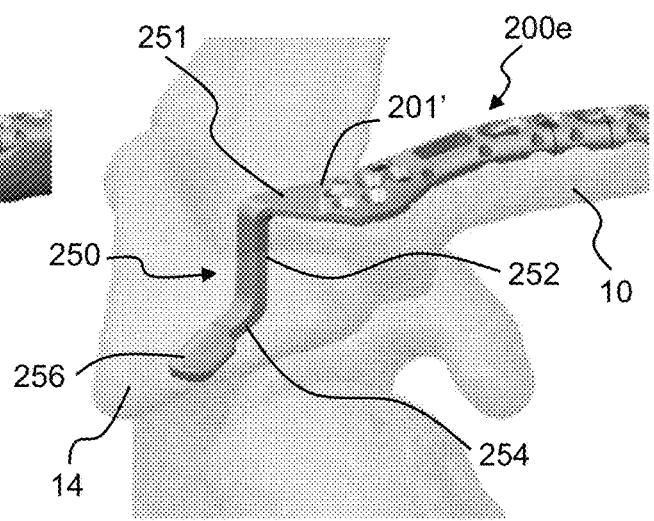
Figure 31A:
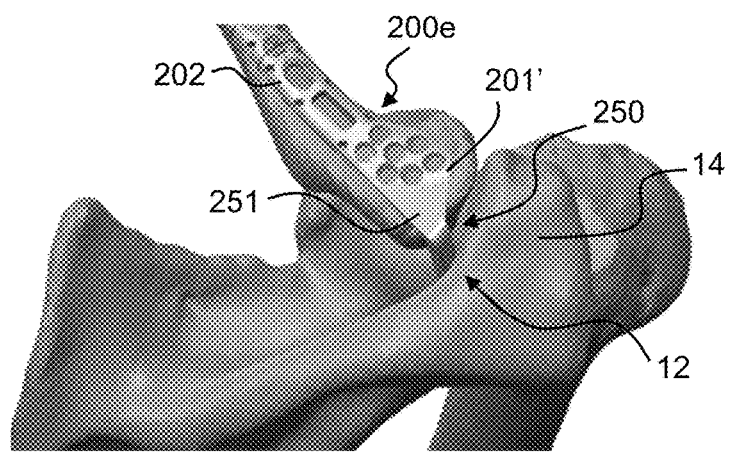
FIGS. 31A and 32A are top perspective views of the hook plate of FIG. 29, with FIG. 32A illustrating the clavicle and AC joint transparently.
Figure 31B:
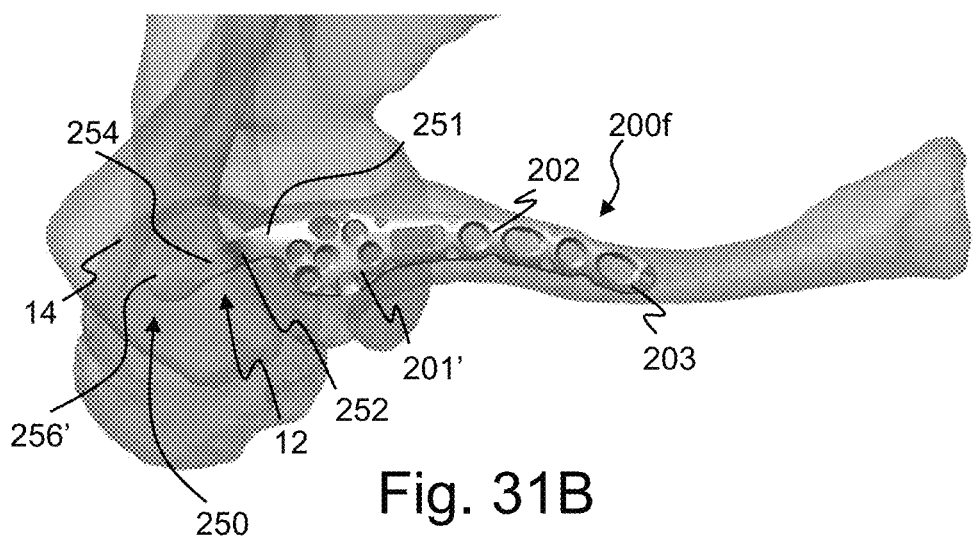
FIGS. 31B and 32B are top perspective views similar to FIGS. 31A and 32A illustrating a hook plate in accordance with another embodiment of the disclosure.
Figure 32A:
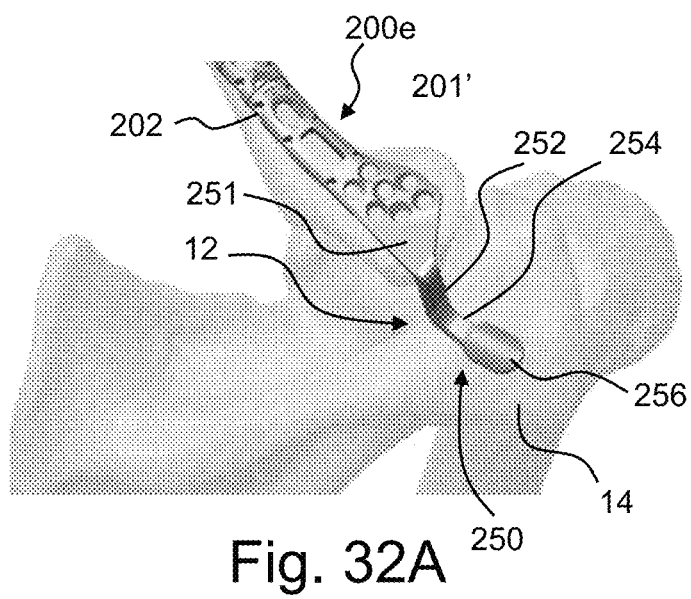
Figure 32B:
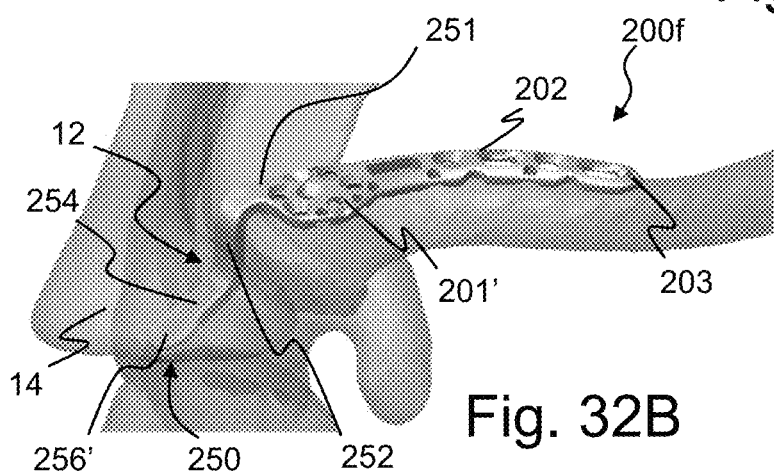
Figure 33A:
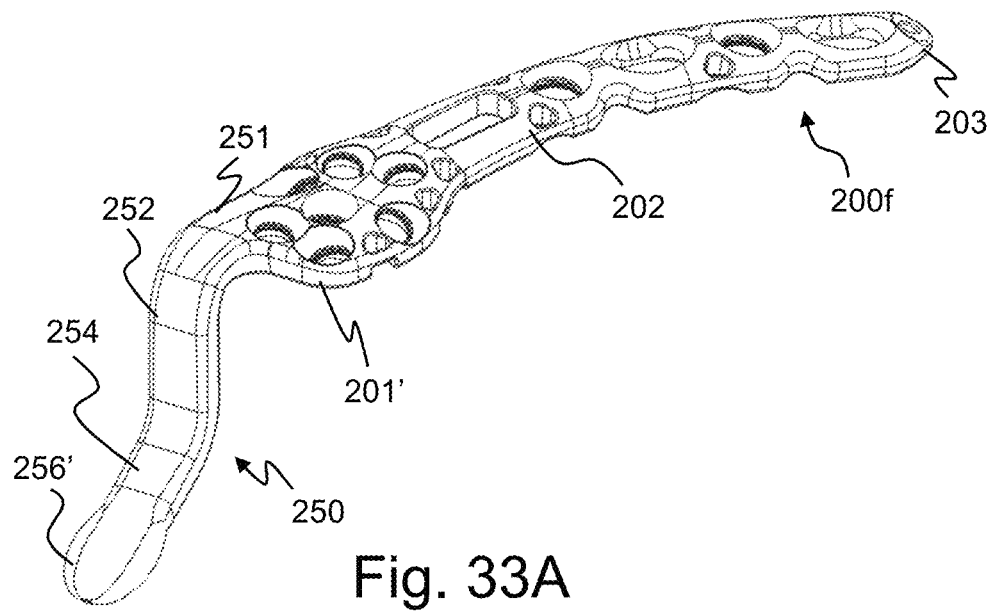
FIGS. 33A, 33B and 33C are a perspective view, top view and side elevation view of the hook plate of FIGS. 31B and 32B.
Figure 33B:
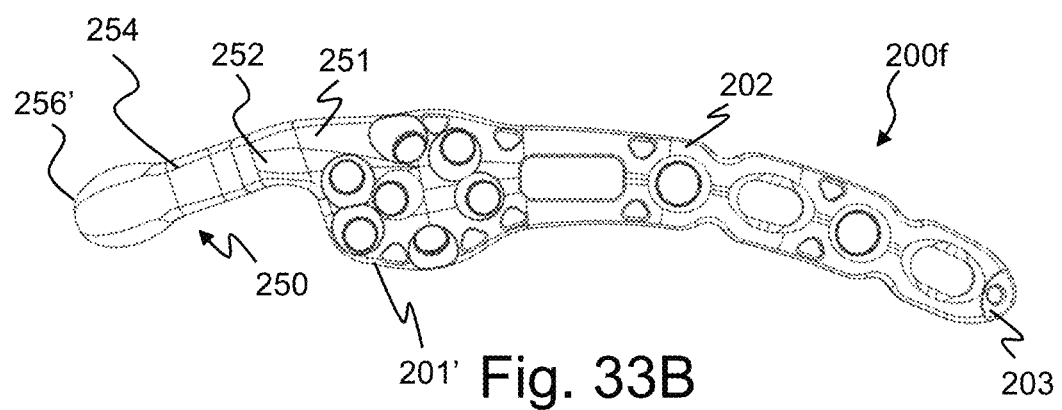
Figure 33C:
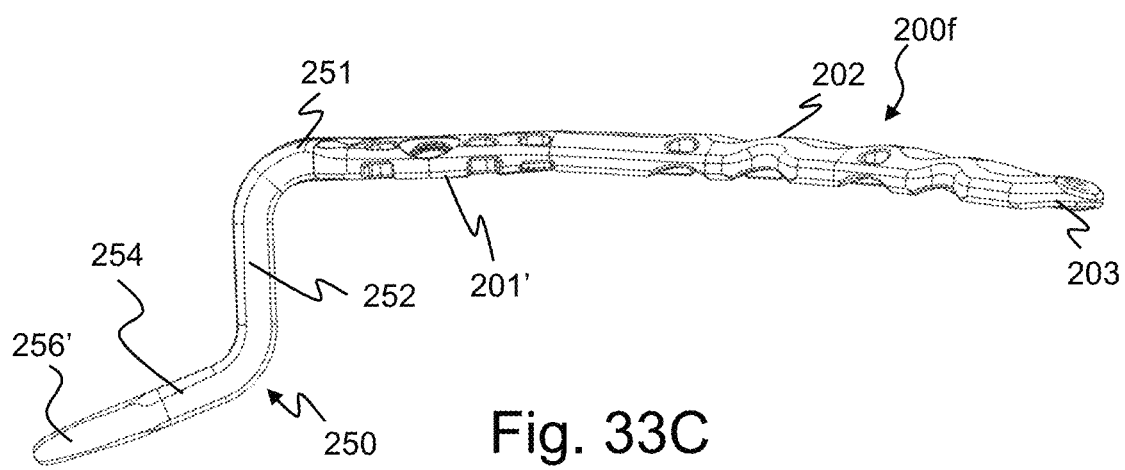

Furthermore, as shown in FIGS. 22-24C, the plates 200a-200d may have varying lengths with varying hole configurations. FIGS. 22 and 23 show superior lateral plates 200a, 200c having a length longer than the length of the superior midshaft plate 200d illustrated in FIGS. 24A-24C. Each of the plates 200a-200d generally include alternating DCP slots 130 and polyaxial holes 136, however, other hole configurations may be utilized. The superior fixation plates 200a and 200b include an additional hole, namely, a sliding slot 240. Referring to FIGS. 25A-25B, the sliding slot 240 has a rectangular configuration and is configured to receive a sliding slot screw 241 with a wide head 242. The shaft of the screw 241 has a diameter smaller than the width of the slot 240 while the head 242 has a diameter greater than the width of the slot 240. The slot 240 allows fine bi-directional adjustments of the plate 200 while maintaining provisional placement. The screw 241 may also be utilized for permanent fixation. The sliding slot screw and all other screws in the set may also be utilized as a stand-alone fragment capture/lag screw.

Referring to FIGS. 22 and 25A-28B, the lateral superior fixation plates 200a, 200b include a lateral extension 210. Such a plate 200a, 200b may be used, for example, to fix fractures occurring at the far lateral end of the clavicle 10. The lateral extension 210 contains a plurality of polyaxial holes 136 that allow many diverging screw trajectories to secure the plate in this thin, metaphyseal bone region, as shown in FIGS. 26A-B. The polyaxial holes 136 accept locking and non-locking screws. For ease of surgical planning, nominal, diverging and converging trajectories are intended to secure in regions of dense bone and away from the acromioclavicular joint space.

The lateral extension 210 also defines a plurality of oblong suture holes 120 similar to those in the shaft of the plate 200a, 200b. The lateral extension suture holes 120 have undercuts 122' to allow free passage of suture underneath the plate 200, however, the width of these undercuts 122' is limited to the width of the suture hole 120.

Referring to FIGS. 29-34B, superior hook plates 200e, 200f will be described. The body 202 of the superior hook plates 200e, 200f is similar to the previous embodiments except that a hook member 250 extends from the end 201' of the plate 200e, 200f. Such hook plates 200e, 200f may, for example, be utilized to aid healing of acromioclavicular (AC) joint separations with clavicular displacement. The hook member 250 includes an extension portion 251 which extends from the end 201' of the plate 200e, 200f to the postero-lateral side of the AC joint 12. A descending arm 252 extends inferiorly from the extension portion 251 to a given depth from which a lateral arm 254 angles laterally to hook underneath the acromion 14. This constrains superior displacement of the clavicle 10. The hook plates are offered with various descending arm 252 lengths to accommodate diverse shoulder and injury anatomies.

Figures 34A, 34B:
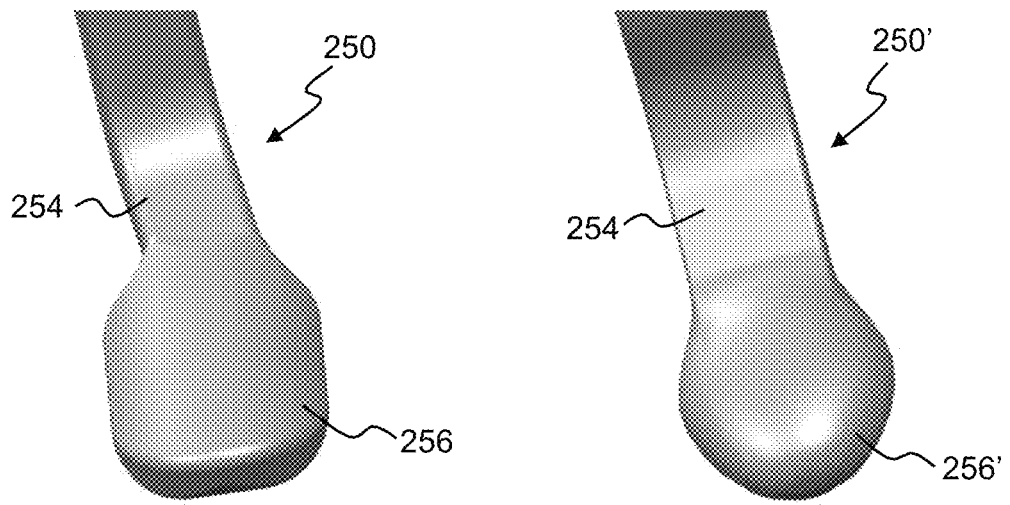
FIGS. 34A and 34B are perspective views of the hook portions of the hook plates in accordance with embodiments of the disclosure.
Figure 35:
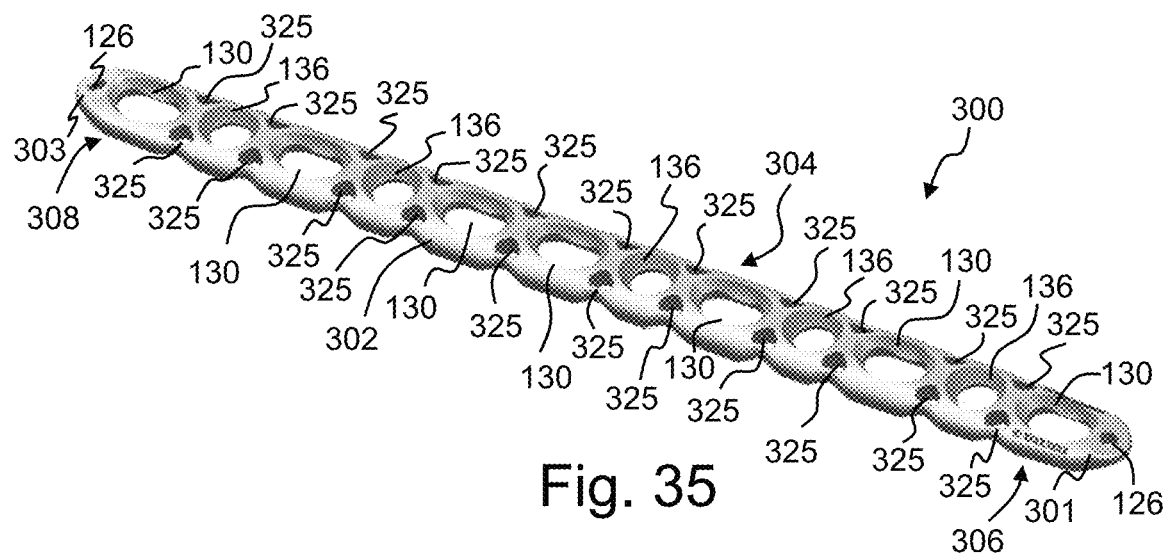
FIG. 35 is a perspective view of a straight fixation plate in accordance with an embodiment of the invention.
Figure 36:
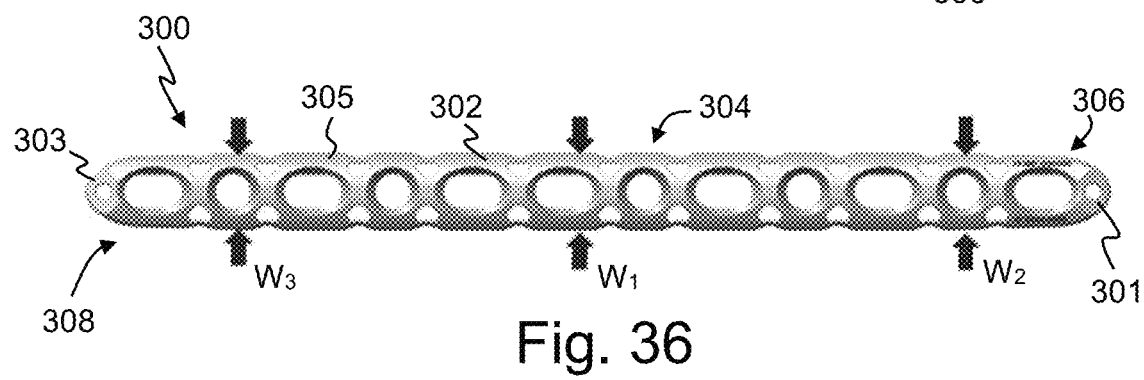
FIG. 36 is a top view of the straight fixation plate of FIG. 35.
Figure 37:
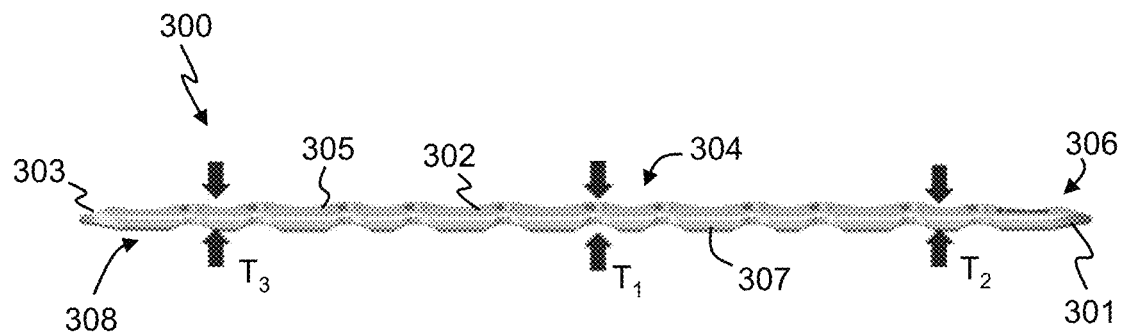
FIG. 37 is a side elevation view of the straight fixation plate of FIG. 35.

In each of the illustrated embodiments, the lateral arm 254 fans out into a widened head 256, 256' that increases contact surface area between the hook member 250 and the underside of the acromion 14. The widened head 256, 256' may have various shapes, with FIGS. 34A and 34B illustrating exemplary shapes. The widened head 256 in FIG. 34A has a curved spatula shape while the widened head 256' in FIG. 34B has a curved spoon shape, each with smoothed edges. The widened heads 256, 256' help to reduce painful irritation, bony erosion, and incidental fracture on the underside of the acromion 14 by distributing the load to a wider area. The smoothed edges of the widened head 256, 256' also facilitate insertion into this soft tissue space and eventual removal, and while in place minimizes irritation to the rotator cuff and other soft tissues.

Referring to FIGS. 35-39, a straight fixation plate 300 in accordance with various embodiments of the disclosure will be described. The straight fixation plates 300 is similar to the anterior and superior fixation plates described above and includes an elongate body 302 extending between opposed ends 301, 303 with an outer surface 305 and an inner, bone contacting surface 307. The straight fixation plates 300 differs from the previously described plates in that the straight fixation plate 300 is not pre-bent, but instead may be configured to be bent to an appropriate curved configuration complementing the curvature of the bone to which it will be attached. That being said, the straight fixation plate 300 may include any of the features described with respect to the anterior and superior plates, including a wider and/or thicker central portion 304, rounded outer and inner surfaces 305, 307, undercuts 112, 114 on the inner surface 307, side relief cuts 116, oblong suture holes 120, undercuts 122, round K-wire holes 126, DCP slots 130 and polyaxial holes 136. The straight fixation plate 300 may have varying lengths with varying hole configurations. The plate 300 generally includes alternating DCP slots 130 and polyaxial holes 136, with the illustrated embodiments having an additional DCP slot 130 in the central region. However, other hole configurations may be utilized.

Figure 38:
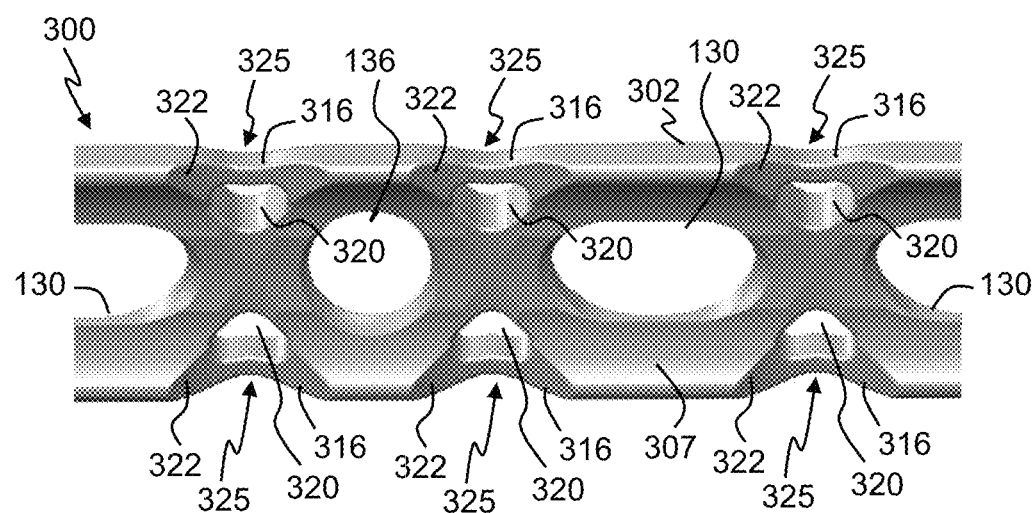
FIG. 38 is a bottom perspective view of a portion of the straight fixation plate of FIG. 35.
Figure 39:
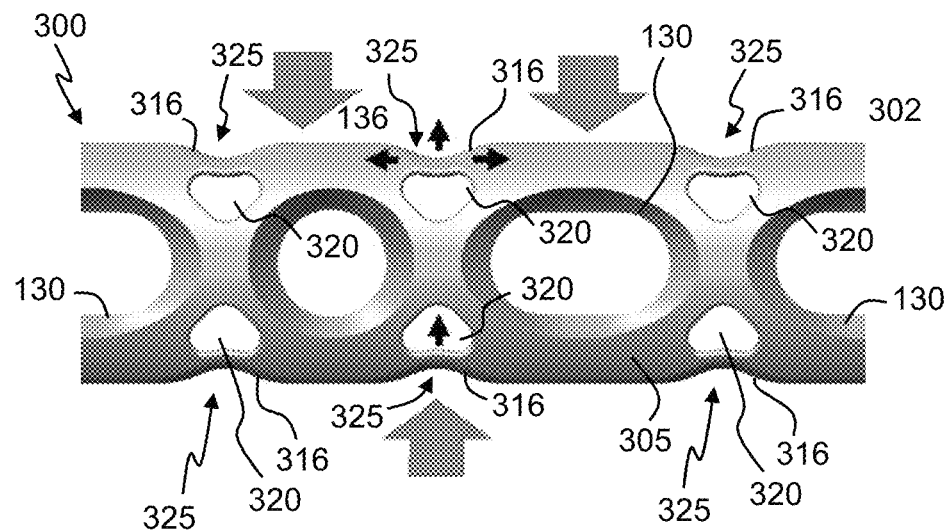
FIG. 39 is an expanded top view of the straight fixation plate of FIG. 35.

The straight fixation plate 300 does not have alternating relief cuts and suture holes like in the previous embodiments, but instead, the holes provide a combined relief cut and suture hole with undercuts. As seen in FIGS. 38 and 39, each combined hole 325 includes a relief cut 316 and undercut 322 into the body 302 in alignment with the oblong suture hole 320. As with the previous embodiments, the relief cut portions 316 are positioned between screw holes thereby reducing the moment of inertia between the screw holes to allow preferential bending between holes, helping to minimize deformation of the screw holes. The illustrated relief cuts 316 have a rounded or smooth configuration to minimize the risk of kinking or fracture. Similar to the previous embodiments, the undercuts 322 also help reduce the moment of inertia between screw holes to allow preferential bending between holes, helping to minimize deformation of screw holes.

Furthermore, the combined holes 325 provide further assistance with bending. More specifically, during surgeon contouring of the plate 300b by bending in the caudal/cranial direction, as illustrated in FIG. 40, the side relief cut 316 of the combined hole 325 on the compression side (bottom side in FIG. 40) will deform, or further "crimp", inwards. The outer edge of the suture hole 320 on the tension side (upper side of FIG. 40) contains more material than is necessary for this span. This tension side will "uncrimp" or deform by necking outwards, resulting in a straighter outer plate edge. Bending to evident failure of the necked material on the tension side may be calibrated to serve as an indicator of excessive bending of the plate 300, making it unusable. The intentional regions of deformation during bending created by the combined holes 325 may diminish bending at undesirable regions at the screw holes.

Referring to FIGS. 41-45, an intramedullary clavicle nail 400 in accordance with an embodiment of the disclosure will be described. A plurality of different sized nails 400, for example, having diameters of 3.0, 3.5, 4.0, 4.5, and 5.0 mm, may be provided as a set. The nails 400 enable minimally invasive treatment of select clavicle fractures. Advantages of this technique are much less incision and scarring, and often elimination of soft tissue prominence.

Figure 45:
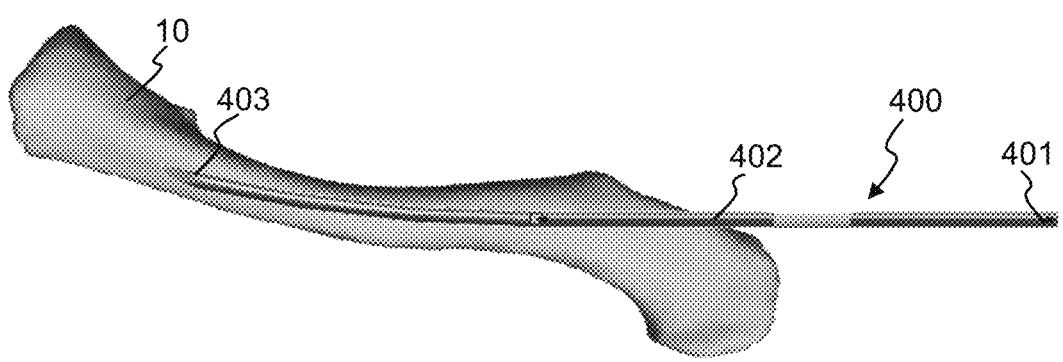
FIG. 45 is a side elevation view of the intramedullary clavicle nail of FIG. 41 positioned within the intramedullary of a clavicle.

Each nail 400 includes an elongated body 402 extending from a trailing end 401 to a medial, leading end 403. The nail body 402 has a pre-contoured configuration with anatomically appropriate radius RM at the medial, leading end 403. The body 402 transitions to a straight region at the trailing end 401. As shown in FIG. 45, upon insertion, the trailing end 401 of the nail 400 exits the posterolateral side of the clavicle 10. The nail 400 is then cut to length and tamped below the bone surface.

Figure 42:
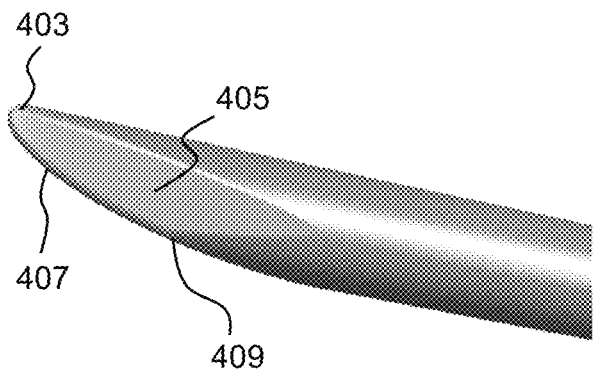
FIG. 42 is a left side perspective view of the tip portion of the intramedullary clavicle nail of FIG. 41.
Figure 43:
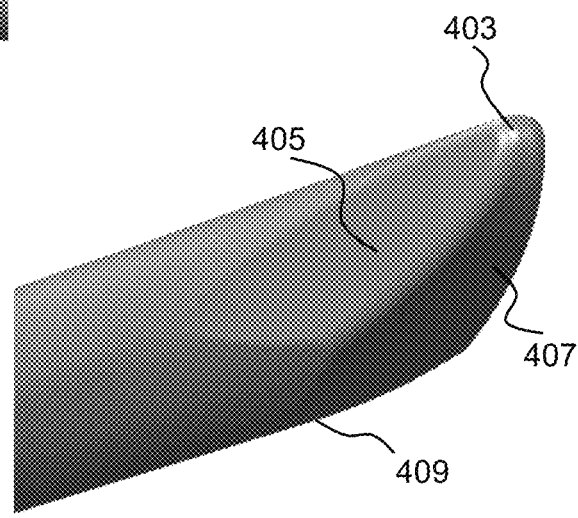
FIG. 43 is a right side perspective view of the tip portion of the intramedullary clavicle nail of FIG. 41.
Figure 44:
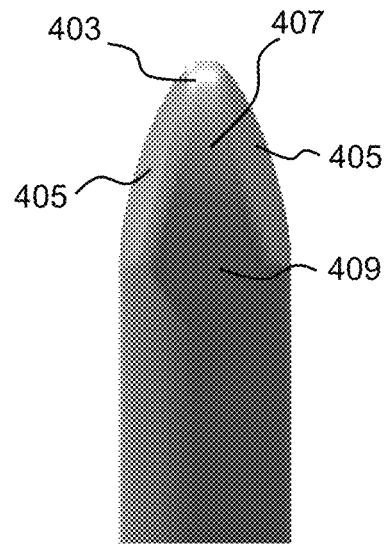
FIG. 44 is a bottom perspective view of the tip portion of the intramedullary clavicle nail of FIG. 41.

Referring to FIGS. 42-44, the leading end 403 of the nail 400 has a pointed shape with flats 405 on each side of a rounded tip 407. The rounded tip 407 extends to a wide underside 409. The pointed shape helps to advance the nail 400 in the medullary canal with minimal pre-drilling, while the wide underside 409 of the tip offers some width to rest against the canal wall. Such resistance helps to provide some rotational stability to maintain the orientation of the pre-curved nail with the restored anterior bone curvature.

The orthopedic bone plates, intramedullary nails, and systems may be particularly useful in the treatment of the clavicle. The devices may be provided with anatomic shapes suitable for fixation at distinct regions of the clavicle. It is envisioned, however, that the features of one embodiment may be combined with features of another embodiment and the disclosure and associated technology can encompass other embodiments not expressly shown or described herein. It will also be appreciated that although generally described with reference to the clavicle, it will be appreciated that the systems and devices may be adapted for use with any long bone, short bone, flat bone, or the like.

While the present disclosure has been described in terms of exemplary aspects, those skilled in the art will recognize that the present disclosure can be practiced with modifications in the spirit and scope of the appended claims. These examples given above are merely illustrative and are not meant to be an exhaustive list of all possible designs, aspects, applications or modifications of the present disclosure.

What is claimed is:

1. A clavicle fixation device comprising:
    an elongated plate extending between first and second ends and defining a central portion, a first end portion between the central portion and the first end, and a second end portion between the central portion and the second end, the elongated plate defining a plurality of spaced apart screw holes,
    wherein at least one pair of relief cuts extends into the elongate plate on opposite sides thereof, the at least one pair of relief cuts axially positioned between a pair of the spaced apart screw holes and at least one pair of suture holes along opposite sides of the elongated plate, the at least one pair of suture holes axially positioned between a pair of the spaced apart screw holes,
    wherein at least one pair of relief cuts and a pair of suture holes define combined holes and a portion of the elongated plate between a relief cut and a suture hole of a combined hole is configured to stretch and straighten when a sufficient tension force is applied to the elongated plate proximate the combined hole.

2. The clavicle fixation device according to claim 1 wherein an undercut in an inner surface of the elongated plate is aligned with each suture hole.

3. The clavicle fixation device according to claim 2 wherein at least a portion of the undercuts have a width larger than a width of a corresponding suture hole.

4. The clavicle fixation device according to claim 1 wherein at least one pair of relief cuts is axially aligned with a pair of suture holes to define combined holes on opposite sides of the elongated plate.

5. The clavicle fixation device according to claim 4 wherein the central portion is sized such that the central portion is configured to overlie a common clavicle fracture zone which is determined based on image research study of clavicle fractures.

6. The clavicle fixation device according to claim 1 wherein a plurality of combined hole pairs are defined along the elongated plate.

7. The clavicle fixation device according to claim 1 wherein the elongated plate has an initial contour configured to compliment a contour of a clavicle anterior or superior surface.

8. The clavicle fixation device according to claim 1 wherein the elongated plate has an initial unbent flat contour.

9. The clavicle fixation device according to claim 1 wherein the second end portion narrows moving from the central portion to the second end.

10. The clavicle fixation device according to claim 1 wherein each of the end portions tapers from a maximum thickness adjacent a central portion to a reduced thickness adjacent the respective end.

11. The clavicle fixation device according to claim 1 wherein the elongated plate defines an outer surface and an inner surface and at least the inner surface has a rounded configuration.

12. The clavicle fixation device according to claim 1 wherein the screw holes include polyaxial holes and dynamic compression plating slots.

13. A clavicle fixation device comprising:
    an elongated plate extending between first and second ends, the elongated plate defining a plurality of spaced apart screw holes,
    wherein at least one pair of relief cuts extends into the elongated plate on opposite sides thereof, the at least one pair of relief cuts axially positioned between a pair of the spaced apart screw holes and at least one pair of suture holes along opposite sides of the elongated plate, the at least one pair of suture holes axially positioned between a pair of the spaced apart screw holes;

wherein at least one pair of relief cuts is axially aligned with a pair of suture holes to define combined holes on opposite sides of the elongated plate; and wherein a portion of the elongated plate between a relief cut and a suture hole of a combined hole is configured to stretch and straighten when a sufficient tension force is applied to the elongated plate proximate the combined hole.

14. The clavicle fixation device according to claim 1 wherein an undercut in an inner surface of the elongated plate is aligned with each suture hole and forms a portion of the combined hole.

15. The clavicle fixation device according to claim 13 wherein the elongated plate has an initial unbent flat contour.

* * * * *